US012642444B1

(12) United States Patent
Schwartz et al.

(10) Patent No.: US 12,642,444 B1
(45) Date of Patent: Jun. 2, 2026

(54) DIAGNOSIS AND TREATMENT OF SMALL VESSEL OCCLUSION USING AN OCCLUDER AND LUMEN TO DISCHARGE FLUID

(71) Applicant: CorFlow Therapeutics AG, Baar (CH)

(72) Inventors: Robert S. Schwartz, Inver Grover Heights, MN (US); Jon Helge Hoem, Baar (CH); Martin T. Rothman, Santa Rosa, CA (US)

(73) Assignee: CorFlow Therapeutics AG, Baar (CH)

( * ) Notice: Subject to any disclaimer, the term of this patent is extended or adjusted under 35 U.S.C. 154(b) by 0 days.

(21) Appl. No.: 19/240,898

(22) Filed: Jun. 17, 2025

Related U.S. Application Data

(60) Continuation of application No. 17/819,580, filed on Aug. 12, 2022, now abandoned, which is a division of
(Continued)

(51) Int. Cl.
*A61B 5/0215* (2006.01)
*A61B 5/00* (2006.01)
(Continued)

(52) U.S. Cl.
CPC .......... *A61B 5/0215* (2013.01); *A61B 5/4848* (2013.01); *A61B 5/6853* (2013.01);
(Continued)

(58) Field of Classification Search
CPC ... A61B 5/0215; A61B 5/4848; A61B 5/6853; A61B 5/02007; A61B 5/6852;
(Continued)

(56) References Cited

U.S. PATENT DOCUMENTS 4,689,041 A     8/1987   Corday et al.
4,722,348 A     2/1988   Ligtenberg et al.
(Continued)

FOREIGN PATENT DOCUMENTS

CN         1182374 A      5/1998
CN      201058169 Y      5/2008
(Continued)

OTHER PUBLICATIONS

AU Application No. 2018336787, Notice of Allowance mailed May 21, 2024; Applicant Corflow Therapeutics AG; 3 pages.
(Continued)

*Primary Examiner* — Kevin C Sirmons
*Assistant Examiner* — Alexandra Lalonde

(57) ABSTRACT

Systems and apparatuses are included that are configured to determine an effectiveness of apparatus and methods used to diagnose and unblock microvascular obstruction (MVO). An infusion system blocks antegrade flow for a short time and measures vascular pressure response as an infusate is infused in stepwise fashion at increasingly higher flow rates. During the antegrade flow occlusion, calculations of a real-time vascular resistance can be obtained using a formula $R(t)=(t)/Qmean(t)$ where: Qmean (t) is flow mean values generated by the infusion system; P(t) is a distal pressure response in a vessel generated from the infusion of the infusate; and R(t) is the calculated real-time vascular resistance using the two other known parameters.

10 Claims, 35 Drawing Sheets

Related U.S. Application Data application No. 16/135,987, filed on Sep. 19, 2018, now Pat. No. 11,412,936.

(60) Provisional application No. 62/560,545, filed on Sep. 19, 2017.

(51) Int. Cl.

| | |
|---|---|
| *A61M 25/09* | (2006.01) |
| *A61M 25/10* | (2013.01) |
| *A61M 25/00* | (2006.01) |

(52) U.S. Cl.
CPC ............ *A61M 25/09* (2013.01); *A61M 25/10* (2013.01); *A61M 2025/0002* (2013.01); *A61M 2025/1052* (2013.01); *A61M 2230/30* (2013.01)

(58) Field of Classification Search
CPC ........... A61B 2017/22067; A61B 2017/00022; A61B 2017/22051; A61B 8/06; A61B 17/12109; A61M 25/09; A61M 25/10; A61M 2025/0002; A61M 2025/1052; A61M 2230/30; A61M 2210/125; A61M 5/142; A61M 2205/3331; A61M 2205/3334; G16H 20/17; G16H 50/20; G16H 40/60
See application file for complete search history.

(56) References Cited

U.S. PATENT DOCUMENTS

| | | | |
|---|---|---|---|
| 4,938,961 | A | 7/1990 | Collins et al. |
| 4,961,738 | A | 10/1990 | Mackin |
| 5,021,045 | A | 6/1991 | Buckberg et al. |
| 5,082,025 | A | 1/1992 | DeVries et al. |
| 5,108,365 | A | 4/1992 | Woods, Jr. |
| 5,182,106 | A | 1/1993 | Mezrow et al. |
| 5,197,485 | A | 3/1993 | Grooters |
| 5,308,320 | A | 5/1994 | Safar et al. |
| 5,324,260 | A | 6/1994 | O'Neill et al. |
| 5,358,481 | A | 10/1994 | Todd et al. |
| 5,370,989 | A | 12/1994 | Stern et al. |
| 5,374,624 | A | 12/1994 | Segel |
| 5,383,854 | A | 1/1995 | Safar et al. |
| 5,423,745 | A | 6/1995 | Todd et al. |
| 5,428,039 | A | 6/1995 | Cohen |
| 5,462,524 | A | 10/1995 | Powell et al. |
| 5,505,698 | A | 4/1996 | Booth et al. |
| 5,552,267 | A | 9/1996 | Stern et al. |
| 5,554,497 | A | 9/1996 | Raymond |
| 5,558,644 | A | 9/1996 | Boyd et al. |
| 5,643,921 | A | 7/1997 | Grover |
| 5,648,071 | A | 7/1997 | Hunter et al. |
| 5,662,607 | A | 9/1997 | Booth et al. |
| 5,670,545 | A | 9/1997 | Horwitz |
| 5,693,462 | A | 12/1997 | Raymond |
| 5,699,793 | A | 12/1997 | Brasile |
| 5,701,905 | A | 12/1997 | Esch |
| 5,702,368 | A | 12/1997 | Stevens et al. |
| 5,716,378 | A | 2/1998 | Minten |
| 5,728,064 | A | 3/1998 | Burns et al. |
| 5,738,096 | A | 4/1998 | Ben-Haim |
| 5,738,649 | A | 4/1998 | Macoviak |
| 5,738,652 | A | 4/1998 | Boyd et al. |
| 5,755,687 | A | 5/1998 | Donlon |
| 5,765,568 | A | 6/1998 | Sweezer, Jr. et al. |
| 5,766,151 | A | 6/1998 | Valley et al. |
| 5,769,812 | A | 6/1998 | Stevens et al. |
| 5,792,094 | A | 8/1998 | Stevens et al. |
| 5,795,325 | A | 8/1998 | Valley et al. |
| 5,799,661 | A | 9/1998 | Boyd et al. |
| 5,800,375 | A | 9/1998 | Sweezer et al. |
| 5,810,757 | A | 9/1998 | Sweezer, Jr. et al. |
| 5,814,016 | A | 9/1998 | Valley et al. |
| 5,820,586 | A | 10/1998 | Booth et al. |
| 5,820,593 | A | 10/1998 | Safar et al. |
| 5,863,366 | A | 1/1999 | Snow |
| 5,868,702 | A | 2/1999 | Stevens et al. |
| 5,868,703 | A | 2/1999 | Bertolero et al. |
| 5,879,316 | A | 3/1999 | Safar et al. |
| 5,879,499 | A | 3/1999 | Corvi |
| 5,885,238 | A | 3/1999 | Stevens et al. |
| 5,906,588 | A | 5/1999 | Safar et al. |
| 5,913,842 | A | 6/1999 | Boyd et al. |
| 5,935,103 | A | 8/1999 | Hill |
| 5,941,894 | A | 8/1999 | Hill |
| 5,997,505 | A | 12/1999 | Hill |
| 6,024,698 | A | 2/2000 | Brasile |
| 6,029,671 | A | 2/2000 | Stevens et al. |
| 6,043,273 | A | 3/2000 | Duhaylongsod |
| 6,046,046 | A | 4/2000 | Hassanein |
| 6,056,723 | A | 5/2000 | Donlon |
| 6,060,454 | A | 5/2000 | Duhaylongsod |
| 6,066,094 | A | 5/2000 | Ben-Haim |
| 6,087,394 | A | 7/2000 | Duhaylongsod |
| 6,090,096 | A | 7/2000 | St. Goar et al. |
| 6,101,412 | A | 8/2000 | Duhaylongsod |
| 6,110,139 | A | 8/2000 | Loubser |
| 6,110,145 | A | 8/2000 | Macoviak |
| 6,127,410 | A | 10/2000 | Duhaylongsod |
| 6,132,397 | A | 10/2000 | Davis et al. |
| 6,139,517 | A | 10/2000 | Macoviak et al. |
| 6,156,005 | A | 12/2000 | Theron |
| 6,165,162 | A | 12/2000 | Safar et al. |
| 6,194,137 | B1 | 2/2001 | Khirabadi et al. |
| 6,210,363 | B1 | 4/2001 | Esch et al. |
| 6,248,086 | B1 | 6/2001 | Sweezer et al. |
| 6,251,093 | B1 | 6/2001 | Valley et al. |
| 6,254,563 | B1 | 7/2001 | Macoviak et al. |
| 6,267,747 | B1 | 7/2001 | Samson et al. |
| 6,285,898 | B1 | 9/2001 | Ben-Haim |
| 6,293,920 | B1 | 9/2001 | Sweezer et al. |
| 6,295,990 | B1 | 10/2001 | Lewis et al. |
| 6,316,403 | B1 | 11/2001 | Pinsky et al. |
| 6,321,909 | B1 | 11/2001 | Wicomb et al. |
| 6,354,999 | B1 | 3/2002 | Dgany et al. |
| 6,361,545 | B1 | 3/2002 | Macoviak et al. |
| 6,371,935 | B1 | 4/2002 | Macoviak et al. |
| 6,398,752 | B1 | 6/2002 | Sweezer, Jr. et al. |
| 6,414,018 | B1 | 7/2002 | Duhaylongsod |
| 6,423,031 | B1 | 7/2002 | Donlon |
| 6,423,032 | B2 | 7/2002 | Parodi |
| 6,426,362 | B1 | 7/2002 | Miller et al. |
| 6,447,443 | B1 | 9/2002 | Keogh et al. |
| 6,451,004 | B1 | 9/2002 | Peters |
| 6,475,186 | B1 | 11/2002 | Safar et al. |
| 6,482,171 | B1 | 11/2002 | Corvi et al. |
| 6,485,450 | B1 | 11/2002 | Owen |
| 6,485,500 | B1 | 11/2002 | Kokish et al. |
| 6,488,671 | B1 | 12/2002 | Constantz et al. |
| 6,491,039 | B1 | 12/2002 | Dobak, III |
| 6,495,532 | B1 | 12/2002 | Bathurst et al. |
| 6,508,777 | B1 | 1/2003 | Macoviak et al. |
| 6,524,339 | B1 | 2/2003 | Adams |
| 6,528,042 | B1 | 3/2003 | Brown et al. |
| 6,540,781 | B2 | 4/2003 | Adams |
| 6,547,760 | B1 | 4/2003 | Samson et al. |
| 6,564,805 | B2 | 5/2003 | Garrison et al. |
| 6,567,679 | B1 | 5/2003 | Khuri et al. |
| 6,569,145 | B1 | 5/2003 | Shmulewitz et al. |
| 6,572,638 | B1 | 6/2003 | Dae et al. |
| RE38,203 | E | 7/2003 | Kelly |
| 6,600,941 | B1 | 7/2003 | Khuri |
| 6,602,276 | B2 | 8/2003 | Dobak, III et al. |
| 6,613,069 | B2 | 9/2003 | Boyd et al. |
| 6,645,197 | B2 | 11/2003 | Garrison et al. |
| 6,669,680 | B1 | 12/2003 | Macoviak et al. |
| 6,673,040 | B1 | 1/2004 | Samson et al. |
| 6,673,041 | B1 | 1/2004 | Macoviak |
| 6,673,042 | B1 | 1/2004 | Samson et al. |
| 6,677,150 | B2 | 1/2004 | Alford et al. |
| 6,685,732 | B2 | 2/2004 | Kramer |
| 6,695,811 | B2 | 2/2004 | Samson et al. |

(56) References Cited

U.S. PATENT DOCUMENTS

| | | | |
|---|---|---|---|
| 6,695,864 B2 | 2/2004 | Macoviak et al. |
| 6,702,773 B1 | 3/2004 | Macoviak et al. |
| 6,711,436 B1 | 3/2004 | Duhaylongsod |
| 6,726,651 B1 | 4/2004 | Robinson et al. |
| 6,740,029 B2 | 5/2004 | Rogers et al. |
| 6,740,484 B1 | 5/2004 | Khirabadi et al. |
| 6,751,492 B2 | 6/2004 | Ben-Haim |
| 6,786,218 B2 | 9/2004 | Dobak, III |
| 6,794,124 B2 | 9/2004 | Steen |
| 6,811,551 B2 | 11/2004 | Dae et al. |
| 6,821,265 B1 | 11/2004 | Bertolero et al. |
| 6,835,188 B2 | 12/2004 | Samson et al. |
| 6,902,545 B2 | 6/2005 | Bertolero et al. |
| 6,902,556 B2 | 6/2005 | Grimes et al. |
| 6,905,494 B2 | 6/2005 | Yon et al. |
| 6,913,600 B2 | 7/2005 | Valley et al. |
| 6,915,149 B2 | 7/2005 | Ben-Haim |
| 6,949,528 B1 | 9/2005 | Goddard et al. |
| 6,949,529 B2 | 9/2005 | Bathurst et al. |
| 6,953,655 B1 | 10/2005 | Hassanein et al. |
| 6,983,179 B2 | 1/2006 | Ben-Haim |
| 6,994,700 B2 | 2/2006 | Elkins et al. |
| 7,001,378 B2 | 2/2006 | Yon et al. |
| 7,017,581 B2 | 3/2006 | Boyd et al. |
| 7,063,679 B2 | 6/2006 | Maguire et al. |
| 7,104,981 B2 | 9/2006 | Elkins et al. |
| 7,157,222 B2 | 1/2007 | Khirabadi et al. |
| 7,176,015 B2 | 2/2007 | Alford et al. |
| 7,238,360 B2 | 7/2007 | Shirwan |
| 7,241,273 B2 | 7/2007 | Maguire et al. |
| 7,259,273 B1 | 8/2007 | Goddard et al. |
| 7,288,089 B2 | 10/2007 | Yon et al. |
| 7,291,144 B2 | 11/2007 | Dobak, III et al. |
| 7,338,434 B1 | 3/2008 | Haarstad et al. |
| 7,364,566 B2 | 4/2008 | Elkins et al. |
| 7,371,254 B2 | 5/2008 | Dobak, III |
| 7,399,272 B2 | 7/2008 | Kim et al. |
| 7,449,018 B2 | 11/2008 | Kramer |
| 7,494,460 B2 | 2/2009 | Haarstad et al. |
| 7,507,235 B2 | 3/2009 | Keogh et al. |
| 7,510,569 B2 | 3/2009 | Dae et al. |
| 7,563,247 B2 | 7/2009 | Maguire et al. |
| 7,572,217 B1 | 8/2009 | Koenig et al. |
| 7,585,836 B2 | 9/2009 | Goodson, IV et al. |
| 7,615,548 B2 | 11/2009 | Gottlieb et al. |
| 7,686,781 B2 | 3/2010 | Vinten-Johansen |
| 7,722,596 B2 | 5/2010 | Shapland et al. |
| 7,758,890 B2 | 7/2010 | Anderson et al. |
| 7,766,961 B2 | 8/2010 | Patel et al. |
| 7,775,988 B2 | 8/2010 | Pijls |
| 7,837,650 B1 | 11/2010 | Cox et al. |
| 7,914,503 B2 | 3/2011 | Goodson, IV et al. |
| 7,951,183 B2 | 5/2011 | Dobak, III |
| 7,993,325 B2 | 8/2011 | Elkins et al. |
| 8,043,283 B2 | 10/2011 | Dobak, III et al. |
| 8,043,351 B2 | 10/2011 | Yon et al. |
| 8,067,150 B2 | 11/2011 | Mangino |
| 8,075,490 B2 | 12/2011 | Charlez |
| 8,076,096 B2 | 12/2011 | Shirwan |
| 8,100,123 B2 | 1/2012 | Belson |
| 8,110,225 B2 | 2/2012 | Anderson et al. |
| 8,128,963 B2 | 3/2012 | Pinsky et al. |
| 8,157,794 B2 | 4/2012 | Dobak, III et al. |
| 8,163,000 B2 | 4/2012 | Dobak, III et al. |
| 8,177,704 B1 | 5/2012 | Mohl et al. |
| 8,281,786 B2 | 10/2012 | Belson |
| 8,292,839 B2 | 10/2012 | O'Neill |
| 8,292,871 B2 | 10/2012 | Shapland et al. |
| 8,317,715 B2 | 11/2012 | Belleville et al. |
| 8,353,942 B2 | 1/2013 | Merrill |
| 8,366,659 B2 | 2/2013 | Ehrenreich et al. |
| 8,398,589 B2 | 3/2013 | Teeslink et al. |
| 8,402,968 B2 | 3/2013 | Belson |
| 8,409,846 B2 | 4/2013 | Hassanein et al. |
| 8,425,549 B2 | 4/2013 | Lenker et al. |
| 8,430,861 B2 | 4/2013 | Schwartz et al. |
| 8,449,449 B2 | 5/2013 | Haarstad et al. |
| 8,454,634 B2 | 6/2013 | Jahns et al. |
| 8,480,650 B2 | 7/2013 | Ehrenreich et al. |
| 8,540,669 B2 | 9/2013 | Ehrenreich et al. |
| 8,567,407 B1 | 10/2013 | Kimani Mwangi et al. |
| 8,568,464 B2 | 10/2013 | Dae et al. |
| 8,578,939 B1 | 11/2013 | Kimani Mwangi et al. |
| 8,585,678 B2 | 11/2013 | Elkins et al. |
| 8,604,072 B2 | 12/2013 | Anderson et al. |
| 8,685,460 B2 | 4/2014 | Anderson et al. |
| 8,702,649 B2 | 4/2014 | Schwartz et al. |
| 8,708,996 B2 | 4/2014 | Consigny et al. |
| 8,715,200 B2 | 5/2014 | Pijls |
| 8,728,747 B2 | 5/2014 | Shirwan |
| 8,734,320 B2 | 5/2014 | Haarstad et al. |
| 8,759,402 B2 | 6/2014 | Gottlieb et al. |
| 8,771,310 B2 | 7/2014 | Forman et al. |
| 8,821,438 B2 | 9/2014 | Ehrenreich et al. |
| 8,822,535 B2 | 9/2014 | Roth et al. |
| 8,876,850 B1 | 11/2014 | Vollmers et al. |
| 8,880,185 B2 | 11/2014 | Hastings et al. |
| 8,888,733 B2 | 11/2014 | Kassab |
| 8,888,737 B2 | 11/2014 | Vaisnys et al. |
| 8,945,039 B2 | 2/2015 | Kassab |
| 8,974,542 B2 | 3/2015 | Fujimoto et al. |
| 8,993,527 B2 | 3/2015 | Mangano |
| 9,004,066 B2 | 4/2015 | Belson |
| 9,012,404 B2 | 4/2015 | Spirio et al. |
| 9,023,010 B2 | 5/2015 | Chiu et al. |
| 9,023,831 B2 | 5/2015 | Bansal |
| 9,040,035 B2 | 5/2015 | Herzberg et al. |
| 9,060,507 B2 | 6/2015 | Alford et al. |
| 9,078,682 B2 | 7/2015 | Lenker et al. |
| 9,078,982 B2 | 7/2015 | Lane et al. |
| 9,155,869 B2 | 10/2015 | Ehrenreich et al. |
| 9,168,361 B2 | 10/2015 | Ehrenreich et al. |
| 9,173,918 B2 | 11/2015 | Zhang et al. |
| 9,174,020 B2 | 11/2015 | Allen et al. |
| 9,205,177 B2 | 12/2015 | Schorgl et al. |
| 9,205,226 B2 | 12/2015 | Allen |
| 9,216,198 B2 | 12/2015 | Balkus, Jr. et al. |
| 9,255,133 B2 | 2/2016 | Shirwan |
| 9,271,964 B2 | 3/2016 | Anderson et al. |
| 9,289,193 B2 | 3/2016 | Argenta et al. |
| 9,314,366 B2 | 4/2016 | Platt et al. |
| 9,320,846 B2 | 4/2016 | Burns et al. |
| 9,326,972 B2 | 5/2016 | Kohn et al. |
| 9,402,952 B2 | 8/2016 | Beyersdorf |
| 9,433,381 B2 | 9/2016 | Mohl et al. |
| 9,433,761 B2 | 9/2016 | Schwartz et al. |
| 9,457,179 B2 | 10/2016 | Hassanein et al. |
| 9,485,983 B2 | 11/2016 | Leybaert |
| 9,492,468 B2 | 11/2016 | Stover |
| 9,504,781 B2 | 11/2016 | Kassab et al. |
| 9,533,124 B2 | 1/2017 | Mack et al. |
| 9,533,127 B2 | 1/2017 | Michal et al. |
| 9,550,046 B1 | 1/2017 | Allen et al. |
| 9,681,875 B2 | 6/2017 | Mohl et al. |
| 9,844,383 B2 | 12/2017 | Allen |
| 9,855,049 B2 | 1/2018 | Schiemanck et al. |
| 9,884,171 B2 | 2/2018 | Ehrenreich et al. |
| 9,999,718 B2 | 6/2018 | Brady et al. |
| 10,010,251 B2 | 7/2018 | Manstrom et al. |
| 10,105,064 B2 | 10/2018 | Manstrom et al. |
| 10,118,016 B2 | 11/2018 | Schwartz et al. |
| 10,238,394 B2 | 3/2019 | Mohl et al. |
| 10,244,951 B2 | 4/2019 | Hiltner |
| 10,279,104 B2 | 5/2019 | Burns et al. |
| 10,313,016 B2 | 6/2019 | Fang et al. |
| 10,315,016 B2 | 6/2019 | Schwartz et al. |
| 10,335,539 B2 | 7/2019 | Burns et al. |
| 10,561,425 B2 | 2/2020 | Schiemanck et al. |
| 10,716,482 B2 | 7/2020 | Anderson et al. |
| 10,835,670 B2 | 11/2020 | Burns et al. |
| 10,842,933 B2 | 11/2020 | Burmaster et al. |
| 10,952,883 B2 | 3/2021 | Hoem et al. |
| 11,135,408 B2 | 10/2021 | Schwartz et al. |
| 11,412,936 B2 * | 8/2022 | Hoem ................... A61B 5/026 |

(56) References Cited

U.S. PATENT DOCUMENTS

| | | | |
|---|---|---|---|
| 11,433,183 | B2 | 9/2022 | Schwartz et al. |
| 11,471,596 | B2 | 10/2022 | Pile-Spellman et al. |
| 11,517,318 | B2 | 12/2022 | Mohl et al. |
| 11,602,618 | B2 | 3/2023 | De Bruyne et al. |
| 11,724,030 | B2 | 8/2023 | Schwartz et al. |
| 11,786,140 | B2 | 10/2023 | Schwartz |
| 11,957,854 | B2 | 4/2024 | Schwartz et al. |
| 12,100,516 | B2 | 9/2024 | Bernard et al. |
| 2001/0041862 | A1 | 11/2001 | Glickman |
| 2002/0045893 | A1 | 4/2002 | Lane et al. |
| 2002/0095147 | A1 | 7/2002 | Shadduck |
| 2002/0115982 | A1 | 8/2002 | Barbut et al. |
| 2003/0018273 | A1 | 1/2003 | Corl et al. |
| 2003/0047777 | A1 | 3/2003 | In't Zandt et al. |
| 2004/0181206 | A1 | 9/2004 | Chiu et al. |
| 2004/0230131 | A1 | 11/2004 | Kassab et al. |
| 2004/0260333 | A1 | 12/2004 | Dubrul et al. |
| 2005/0049451 | A1 | 3/2005 | Schock et al. |
| 2005/0059931 | A1 | 3/2005 | Garrison et al. |
| 2005/0245894 | A1 | 11/2005 | Zadno-Azizi |
| 2005/0245897 | A1 | 11/2005 | Bolduc et al. |
| 2005/0267561 | A1 | 12/2005 | Jones et al. |
| 2006/0184089 | A1 | 8/2006 | Makower et al. |
| 2008/0300573 | A1 | 12/2008 | Consigny et al. |
| 2009/0177183 | A1 | 7/2009 | Pinkernell et al. |
| 2010/0121204 | A1 | 5/2010 | Utsuno et al. |
| 2010/0143317 | A1 | 6/2010 | Pecora et al. |
| 2010/0168649 | A1 | 7/2010 | Schwartz et al. |
| 2010/0249704 | A1 | 9/2010 | Wagner |
| 2010/0280451 | A1 | 11/2010 | Teeslink et al. |
| 2011/0040319 | A1 | 2/2011 | Fulton, III |
| 2011/0196255 | A1 | 8/2011 | Kassab |
| 2012/0072190 | A1 | 3/2012 | Sharma et al. |
| 2012/0157913 | A1 | 6/2012 | Aziz et al. |
| 2012/0265079 | A1 | 10/2012 | Hilmersson |
| 2012/0265283 | A1 | 10/2012 | Mack et al. |
| 2012/0276152 | A1 | 11/2012 | Hossainy et al. |
| 2013/0035560 | A1 | 2/2013 | Anand et al. |
| 2013/0131523 | A1 | 5/2013 | Suchecki et al. |
| 2013/0132054 | A1 | 5/2013 | Sharma et al. |
| 2013/0150737 | A1 | 6/2013 | Schwartz et al. |
| 2013/0165858 | A1 | 6/2013 | Cox et al. |
| 2013/0282097 | A1 | 10/2013 | Burton |
| 2014/0155684 | A1 | 6/2014 | Ehrenreich |
| 2014/0323887 | A1 | 10/2014 | Anderson et al. |
| 2015/0018928 | A1 | 1/2015 | Sachar et al. |
| 2015/0133799 | A1 | 5/2015 | O'Connell et al. |
| 2015/0141853 | A1 | 5/2015 | Miller, III et al. |
| 2016/0082178 | A1 | 3/2016 | Agah et al. |
| 2016/0199003 | A1 | 7/2016 | McCaffrey et al. |
| 2016/0213834 | A1 | 7/2016 | Brady et al. |
| 2016/0270731 | A1 | 9/2016 | Burkett |
| 2016/0361068 | A1 | 12/2016 | Mohl et al. |
| 2016/0367785 | A1 | 12/2016 | Schwartz et al. |
| 2017/0119260 | A1 | 5/2017 | Gilbert |
| 2017/0189654 | A1* | 7/2017 | Schwartz ............ A61M 5/1723 |
| 2017/0290598 | A1 | 10/2017 | Culbert et al. |
| 2018/0085519 | A1 | 3/2018 | McCaffrey et al. |
| 2018/0146864 | A1 | 5/2018 | Jansen et al. |
| 2018/0185576 | A1 | 7/2018 | Burns et al. |
| 2018/0280172 | A1 | 10/2018 | Hoem et al. |
| 2018/0353681 | A1 | 12/2018 | Burmaster et al. |
| 2019/0046760 | A1 | 2/2019 | Schwartz et al. |
| 2019/0078914 | A1 | 3/2019 | Doering et al. |
| 2019/0082976 | A1 | 3/2019 | Hoem et al. |
| 2019/0275248 | A1 | 9/2019 | Schwartz et al. |
| 2019/0290889 | A1 | 9/2019 | De Bruyne et al. |
| 2019/0358437 | A1 | 11/2019 | Schwartz et al. |
| 2020/0093991 | A1 | 3/2020 | Schwartz et al. |
| 2020/0282189 | A1 | 9/2020 | Gaynor |
| 2020/0284632 | A1 | 9/2020 | Abed et al. |
| 2020/0284668 | A1 | 9/2020 | Razavidinani et al. |
| 2020/0284675 | A1 | 9/2020 | Jamali |
| 2020/0284677 | A1 | 9/2020 | Wagner |
| 2020/0316348 | A1 | 10/2020 | Ascher et al. |
| 2020/0383688 | A1 | 12/2020 | Olson et al. |
| 2021/0085932 | A1 | 3/2021 | Oezer |
| 2021/0228387 | A1 | 7/2021 | Hoem et al. |
| 2021/0361170 | A1 | 11/2021 | Schwartz et al. |
| 2021/0366620 | A1 | 11/2021 | Bernard et al. |
| 2022/0016399 | A1 | 1/2022 | Schwartz et al. |
| 2022/0062214 | A1 | 3/2022 | Pantos et al. |
| 2022/0218210 | A1 | 7/2022 | Schwartz et al. |
| 2022/0378301 | A1 | 12/2022 | Schwartz et al. |
| 2023/0381415 | A1 | 11/2023 | Schwartz et al. |
| 2024/0269440 | A1 | 8/2024 | Schwartz et al. |

FOREIGN PATENT DOCUMENTS

| | | |
|---|---|---|
| CN | 101356286 A | 1/2009 |
| CN | 102125721 A | 7/2011 |
| CN | 102596010 A | 7/2012 |
| CN | 102740902 A | 10/2012 |
| CN | 102811758 A | 12/2012 |
| CN | 103153212 A | 6/2013 |
| CN | 103228317 A | 7/2013 |
| CN | 103298441 A | 9/2013 |
| CN | 103826690 A | 5/2014 |
| CN | 105636512 A | 6/2016 |
| CN | 105848573 A | 8/2016 |
| CN | 105879008 A | 8/2016 |
| CN | 106132309 A | 11/2016 |
| CN | 106310495 A | 1/2017 |
| EP | 0363203 A2 | 4/1990 |
| EP | 0405831 A2 | 1/1991 |
| EP | 2497520 A1 | 9/2012 |
| EP | 2793992 B1 | 9/2015 |
| EP | 2073884 B1 | 10/2018 |
| EP | 3705034 A1 | 9/2020 |
| GB | 2541368 A | 2/2017 |
| GB | 2577472 A | 4/2020 |
| JP | H10500587 A | 1/1998 |
| JP | H11178929 A | 7/1999 |
| JP | 2006187620 A | 7/2006 |
| JP | 2008173137 A | 7/2008 |
| JP | 2008264134 A | 11/2008 |
| JP | 2009514596 A | 4/2009 |
| JP | 2009233175 A | 10/2009 |
| JP | 2012200573 A | 10/2012 |
| JP | 2013146505 A | 8/2013 |
| JP | 2013534845 A | 9/2013 |
| JP | 2014069034 A | 4/2014 |
| JP | 2015522347 A | 8/2015 |
| JP | 2016507272 A | 3/2016 |
| JP | 2016168151 A | 9/2016 |
| JP | 2016215836 A | 12/2016 |
| WO | WO-1996000596 A1 | 1/1996 |
| WO | WO-1999044666 A2 | 9/1999 |
| WO | WO-2001028419 A2 | 4/2001 |
| WO | WO-2001070325 A2 | 9/2001 |
| WO | WO-2002085443 A1 | 10/2002 |
| WO | WO-2004062526 A2 | 7/2004 |
| WO | WO-2004080508 A2 | 9/2004 |
| WO | WO-2006059317 A1 | 6/2006 |
| WO | WO-2008088579 A2 | 7/2008 |
| WO | WO-2010105356 A1 | 9/2010 |
| WO | WO-2013055896 A1 | 4/2013 |
| WO | WO-2014022935 A1 | 2/2014 |
| WO | WO-2014106158 A1 | 7/2014 |
| WO | WO-2015108928 A1 | 7/2015 |
| WO | WO-2015150913 A2 | 10/2015 |
| WO | WO-2017004432 A1 | 1/2017 |
| WO | WO-2017078693 A1 | 5/2017 |
| WO | WO-2017078694 A1 | 5/2017 |
| WO | WO-2017120229 A1 | 7/2017 |
| WO | WO-2017160270 A1 | 9/2017 |
| WO | WO-2017210584 A1 | 12/2017 |
| WO | WO-2018175485 A1 | 9/2018 |
| WO | WO-2019060421 A1 | 3/2019 |
| WO | WO-2019173758 A1 | 9/2019 |
| WO | WO-2019232452 A1 | 12/2019 |
| WO | WO-2020061507 A1 | 3/2020 |
| WO | WO-2021035190 A1 | 2/2021 |

(56)                     References Cited

FOREIGN PATENT DOCUMENTS

| WO | WO-2021234670 A1 | 11/2021 |
|----|------------------|---------|
| WO | WO-2022147318 A1 | 7/2022  |
| WO | WO-2022149106 A1 | 7/2022  |

OTHER PUBLICATIONS

AU Application No. 2018336787, Office Action mailed Jul. 31, 2023; Applicant Corflow Therapeutics AG; 3 pages.

CA Application No. 3076035, Office Action mailed Nov. 29, 2024; Applicant Corflow Therapeutics AG; 3 pages.

Chung et al. "Microfluidic fabrication of microengineered hydrogels and their application in tissue engineering." Lab on a Chip. 2012;12(1):45-59.

CN Application No. 201880070198.7, Notice of Allowance mailed Mar. 12, 2024; Applicant Kofoza Medical Company; with English translation 3 pages.

CN Application No. 201880070198.7, Office Action mailed Mar. 1, 2023; Applicant Kofoza Medical Company; with English translation 13 pages.

CN Application No. 201880070198.7, Office Action mailed Oct. 20, 2023; Applicant Kofoza Medical Company; with English translation 8 pages.

Costa et al. "Mimicking arterial thrombosis in a 3D-printed microfluidic in vitro vascular model based on computed tomography angiography data". Lab on a Chip. 2017;17(16):2785-2792.

EP Application No. 18793291.8, Office Action mailed Jun. 21, 2023; Applicant Corflow Therapeutics AG; 6 pages.

JP Application No. 2020-537457, Notice of Allowance mailed Feb. 10, 2023; Applicant Corflow Therapeutics AG; with English translation 5 pages.

JP Application No. 2020-537457, Office Action mailed Sep. 12, 2022; Applicant Corflow Therapeutics AG; with English translation 41 pages.

Kim et al. "Vasculature-on-a-chip for in vitro disease models." Bioengineering. Jan. 2, 20174;4(1):8; 18 pages.

Lindsey et al. "Guidelines for experimental models of myocardial ischemia and infarction." American Journal of Physiology-Heart and Circulatory Physiology. Apr. 1, 2018;314(4):H812-H838.

Liu J. "Coronary Heart Disease: Anatomy, Function and Imaging." Peking Union Medical College Press. Apr. 2013. 30, p. 56.

Malinowski et al. "Large animal model of acute right ventricular failure with functional tricuspid regurgitation." International Journal of Cardiology. Aug. 1, 2018;264:124-129.

Meier et al. "Coronary wedge pressure in relation to spontaneously visible and recruitable collaterals." Circulation. May 1987;75(5):906-913.

PCT Application No. PCT/US2018/051760, International Preliminary Report on Patentability mailed Apr. 2, 2020, Applicant Corflow Therapeutics AG; 9 pages.

PCT Application No. PCT/US2018/051760, International Search Report and Written Opinion mailed Jan. 3, 2019, Applicant HOEM, Jon Helge et al.; 13 pages.

Qiu et al. "Microvasculature-on-a-chip for the long-term study of endothelial barrier dysfunction and microvascular obstruction in disease." Nature Biomedical Engineering. Jun. 2018;2(6):453-463.

Tsai et al. "In Vitro modeling of the microvascular occlusion and thrombosis that occur in hematologic diseases using microfluidic technology." Journal of Clinical Investigation. Dec. 12, 2011;122(1); 408-418.

Urban et al. "Coronary wedge pressure: a predictor of restenosis after coronary balloon angioplasty." Journal of the American College of Cardiology. Sep. 1987;10(3):504-509.

U.S. Appl. No. 16/135,987, Final Office Action mailed May 26, 2021; Inventor Hoem, Jon Helge et al.; 10 pages.

U.S. Appl. No. 16/135,987, Non-Final Office Action mailed Dec. 9, 2021; Inventor Hoem, Jon Helge et al.; 9 pages.

U.S. Appl. No. 16/135,987, Non-Final Office Action mailed Feb. 9, 2021; Inventor Hoem, Jon Helge et al.; 10 pages.

U.S. Appl. No. 16/135,987, Notice of Allowance mailed Mar. 30, 2022; Inventor Hoem, Jon Helge et al.; 8 pages.

U.S. Appl. No. 17/819,580, Non-Final Office Action mailed Dec. 18, 2024; Inventor Schwartz, Robert S et al.; 18 pages.

Wahab A. "Interpolation and Extrapolation." Proc. Topics Syst. Eng. Jan. 2017;17:1-6.

* cited by examiner

100

200

600

Angiographic No-ReFlow after 90min LAD occlusion distal to the 2$^{nd}$ diagonal

700

2 Ch hi-resolution gadolinium
enhanced MRI scan with MVO

800

Platelet Rich Microvascular Obstruction in a 200μm Vessel

2Ch

902

4Ch

900

1200

| | n | MVO AVG (% of LV Mass) |
|---|---|---|
| CorFlow Porcine MVO Model | 15 | 2.34±1.07% (1.27 – 3.41%) |
| Human Data (STEMI Pts.)[1] | 348 | 1.9% (0.9 - 3.9%) |

FIG. 12

| No. | Animal | MVO Present? | Infarct Size [%] | MVO [%] |
|---|---|---|---|---|
| 1 | 8 | yes | 21.6 | 4.7 |
| 2 | 9 | yes | 23.1 | 1 |
| 3 | 10 | yes | 23.9 | 2.4 |
| 4 | 11 | yes | 13.0 | 1.4 |
| 5 | 12 | yes | 20.4 | 2.8 |
| 6 | 13 | yes | 21.8 | 3.4 |
| 7 | 14 | no | No infarct or MVO | |
| 8 | 15 | yes | 20.8 | 3.4 |
| 9 | 16 | yes | 19.5 | 1.6 |
| 10 | 17 | yes | 26.2 | 2.8 |
| 11 | 18 | yes | Cardiologist training | |
| 12 | 19 | yes | 20.1 | 2.3 |
| 13 | 20 | yes | 18.1 | 2.4 |
| 14 | 21 | yes | 25.1 | 1.3 |
| 15 | 22 | yes | 28.9 | 2.5 |
| 16 | 23 | yes | 6.2 | 0.8 |
| Mean | | | 20.62 | 2.34 |
| SDEV | | | 5.64 | 1.07 |
| Count | | | 14 | 14 |

1400

Apical levels 14 and 15

Myocardial infarction (MI), with capillary congestion and endothelial cell swelling. There is perivascular oedema, 100 um Ø arteries appear swollen (arrow)

2200

2202

2201 block 8 (level 14, apical region):
thrombus. Closer view block 8 (level 14, apical region), 200 μm
further: thrombus is not longer there

2400

2401

2402

Photomicrograph of postmortem specimen in the
region of infarct. Arrows show two small blood vessels com-
pletely obstructed from platelet-fibrin thrombus. This micro-
scopic examination confirms microvascular obstruction as pre-
dicted by CMRI scan.

3104

| Reported measurement / Test conducted | Flow rate 5 ml/min n=? | Baseline to ml/min n=? | Flow rate 24 ml/min n=? | Flow rate 48 ml/min n=? | Flow rate 48 ml/min n=? |
|---|---|---|---|---|---|
| p-value Baseline to 10min reperfusion | 0.016 | 0.002 | 0.001 | 0.001 | <0.001 |
| p-value Baseline to 4h reperfusion | 0.026 | <0.001 | <0.001 | 0.001 | 0.001 |

DIAGNOSIS AND TREATMENT OF SMALL VESSEL OCCLUSION USING AN OCCLUDER AND LUMEN TO DISCHARGE FLUID

This application is a continuation of U.S. patent application Ser. No. 17/819,580, filed Aug. 12, 2022, which is a divisional of U.S. patent application Ser. No. 16/135,987, filed Sep. 19, 2018, now U.S. Pat. No. 11,412,936, which claims priority and the benefit of U.S. Provisional Patent Application No. 62/560,545, filed Sep. 19, 2017 the entire contents of each of which are hereby incorporated by reference herein in their entirety.

TECHNICAL FIELD

Methods and devices for the diagnosis and treatment of microvascular obstruction (MVO) and other dysfunctional diseases of the microvasculature of many organs including the heart.

BACKGROUND

Heart attack or STEMI ('STEMI' defined as acute ECG ST segment myocardial infarction) is caused by sudden occlusion of an epicardial coronary artery, typically by fibrin and platelet rich clot, with associated and embolic plaque and debris. Electrocardiographic signs of acute transmural myocardial infarction (heart attack) are ECG tracings with ST segment elevation (STEMI). ST segment elevation is a hallmark of severe coronary artery narrowing, often with occlusion causing ongoing ischemic myocardial injury with cell death. Large vessel occlusion is often associated with small vessel or stenosis occlusion (termed microvascular occlusion or MVO) by clot and embolic debris is also a serious problem since the heart muscle is deprived of blood, oxygen, and critical nutrients necessary to sustain cell life.

Interventional cardiology is very proficient at opening severely narrowed or occluded epicardial coronary arteries in the cardiac catheterization laboratory using catheters, guide wires, balloons, and stents. However, microvascular obstruction cannot be diagnosed in the catheter lab, and more importantly MVO cannot be treated even if/when it could be accurately diagnosed.

Heart muscle salvage (saving muscle from death due to lack of blood and oxygen) is a critical concern to ensure good long-term outcomes in patients suffering STEMI. A key component of good long-term outcome involves minimizing the time between coronary artery occlusion (at home or outside the hospital) and opening the occluded artery in the catheter lab. Interventional cardiologists can reduce artery occlusion time by implementing streamlined and efficient emergency medical systems whose goal is to have STEMI patients arrive in catheterization laboratory as soon as possible, avoiding long term STEMI complications. Complications resulting from STEMI and MVO include, systolic and diastolic heart failure, arrhythmias, aneurysms, ventricular rupture and multiple other serious complications. These complications can markedly shorten life and impose severe limitations on quality of life.

Modern interventional therapy for acute myocardial infarction has matured over time with impressive clinical results. Heart attack/STEMI death rates at 30 days have dropped from more than 30% to less than 5%, achieved by reperfusing the heart with blood as soon as possible during coronary arterial occlusion. This goal is accomplished by streamlining clinical care systems to open coronary arteries in the catheterization lab as rapidly as possible after heart attack onset. Emergency procedures including stenting and balloon angioplasty are undisputed as necessary for improving early and late clinical results of acute heart attack therapy.

However, substantial challenges remain for treating STEMI patients and reducing long term complications. These problems include heart failure (poor cardiac function and cardiac enlargement), cardiac/ventricular rupture, persistent ischemic chest pain/angina, left ventricular aneurysm and clot, and malignant arrhythmias.

Late Heart failure complicates 25-50% of acute STEMI, caused by poor left ventricular function and damaged myocardium. Heart failure is worsened as the heart remodels in shape and size, and loses function. Nearly half of all new heart failure in patients under 75 years is linked to STEMI.

Many years investigating STEMI therapy show that opening the epicardial/large coronary artery is insufficient to salvage heart muscle and optimize long term patient outcome. The most common reason for poor late results after heart attack is microvascular obstruction (MVO). MVO is occlusion or severe flow limitation in the internal cardiac microvessels, typically by clot. These microvessels are impervious to stenting and conventional thrombolytic therapy. Thus, despite a widely patent epicardial coronary artery, residual MVO obstructs blood flow into the heart causing cell ischemia death from severe heart muscle damage.

MVO thus remains a critical frontier in cardiology. Cardiac microvessels comprise small arteries, arterioles, capillaries and venules which are frequently filled with clot and debris (platelets, fibrin, and embolic plaque material) during STEMI. Too often, obstructed microvessels (MVO) do not resolve even after stent placement, and have serious long-term negative prognostic implications.

MVO is very common in STEMI patients, even though stenting and balloon angioplasty are successful at opening epicardial coronary arteries. MVO occurs in more than half of all STEMI patients, even with good blood flow through open epicardial arteries and newly placed stents.

MVO extent is key to the severity of myocardial damage and patient outcome. MVO is best imaged via cardiac MRI which measures MVO location, extent and severity. MRI, however, cannot be performed emergently or during a cardiac catheterization procedure since it requires patients to be in a separate imaging area and within a separate scanner.

Important features of MVO may be summarized by the following:

1. MVO and microvascular dysfunction in STEMI is the principal cause of major complications early and late after heart attack.

2. Angiographic "no-reflow" or "low-reflow" is caused by MVO and is due to obstructed microvessels within the heart. MVO is fluoroscopically characterized by very slow X-ray contrast filling the epicardial coronary arteries as visualized during coronary treatment in the catheterization laboratory.

3. MVO causes myocardial cell injury and death from prolonged ischemia/lack of oxygen, blood, and key metabolic nutrients such as glucose. MVO microscopic analysis shows microvessels filled with platelet and fibrin clot, dead myocardial cells, inflammatory cells, myocyte cell death, and endothelial cell death along the obstructed intramyocardial capillaries.

4. MVO studied acutely shows cardiac arterioles and capillaries completely occluded by platelet and fibrin-rich thrombus, platelet-neutrophil aggregates, dying blood cells and embolic debris.

5. When MVO complicates acute STEMI/myocardial infarction, far greater heart/myocardial damage occurs, and poor ventricular function occurs early.

6. MVO is very common. It occurs in:

a. 53% of all STEMI and NSTEMI regardless of epicardial flow, b. 90% of Large Transmural STEMI, c. 40% of MI with TIMI III (normal) X-ray visualized flow, and d. MVO is the single most potent prognostic marker of events after controlling for infarct size.

7. Patients with microvascular obstruction have more late major adverse cardiovascular events (MACE) than those without MVO (45% versus 9%).

8. MVO is the best predictor of acute and chronic cardiovascular adverse outcomes.

9. MVO acutely becomes late fibrous scar and causes poor cardiac function.

MVO cannot be diagnosed in a conventional catheterization laboratory. Moreover, no effective conventional therapies were available. Many possible prior therapies all proved essentially ineffective, and in some cases, dangerous.

Problems encountered with prior MVO therapy include rapid fluid bolus injection with drugs. This failure is best understood as fluids follow paths of least resistance. MVO-obstructed vessels have very slow flow, with very high hydraulic resistance. Direct drug bolus into coronary arteries has little effect against MVO because the injected agent enters only open and unobstructed microchannels, with little or none entering obstructed microvessels in STEMI. Studies suggest that only $\frac{1}{1000}$ of a locally injected drug enters obstructed microvessels, most drug entering the open and unobstructed microvessels. Delivering high drug doses to occluded microchannels in this adverse ratio yields unacceptably high toxic systemic drug level because all injected drug eventually enters the systemic circulation. High systemic drug levels place patients at risk of dangerous systemic bleeding and other systemic complications including vessel dissection due to high flow infusion rates.

Solving MVO is a critical need for cardiologists. Technology and methods to successfully and efficiently deliver therapeutic agents to MVO-obstructed microvessels of multiple organs (Heart, brain, bowel, extremities, liver, and kidneys for example) are not available. Such therapy must be simple, efficient, safe, and easy to use in the catheterization lab. Such methods must deliver high dose therapeutic agents into occluded channels without causing toxic systemic concentrations, and to be available to treat microvessels after flow restoration will permit a further goal of preventing or limiting reperfusion injury.

There is a need in the art for apparatus and methods that can measure real-time intracoronary vascular resistance (RTIVR) and compliance to diagnose and treat microvascular obstruction (MVO) and tissue necrosis/infarction.

SUMMARY

Methods and devices for the diagnosis and treatment of microvascular obstruction (MVO) and other dysfunctional diseases of the microvasculature of many organs including the heart. More particularly, non-limiting embodiments include novel devices and methods to successfully diagnose, restore patency, open and preserve flow, and limit reperfusion injury in organs and cases with microvascular obstruction. No known prior art methods are available to detect and measure or treat MVO in real time during scenarios such as invasive angiographic/therapeutic procedures. Such procedures include therapy for organ systems including the heart (acute myocardial infarction-primary percutaneous coronary intervention (PPCI)), brain (stroke (CVA), bowel ischemia/infarction, pulmonary emboli/infarction, critical limb ischemia/infarction, renal ischemia/infarction, and others. Using methods of the invention, a system comprising specialized infusion and sensing catheter, diagnostic agents, therapeutic agents, and control console with specialized algorithms can both diagnose and treat MVO by eliminating the microvascular clot and debris causing the obstruction. The techniques involve a combination of novel devices, methods, and software to simultaneously diagnose and treat MVO. This permits operation in real-time with real-time operator feedback for diagnostic and therapeutic decision making, and so create a system feasible for interventional procedures.

BRIEF DESCRIPTION OF THE DRAWINGS

The present disclosure is illustrated by way of example and not limitation in the figures of the accompanying drawings, in which like references indicate similar elements and in which:

FIG. 12 illustrates a table comparing results of a porcine non-clinical trial to human data, in accordance with some embodiments of the present subject matter;

SUMMARY

Figure 1:
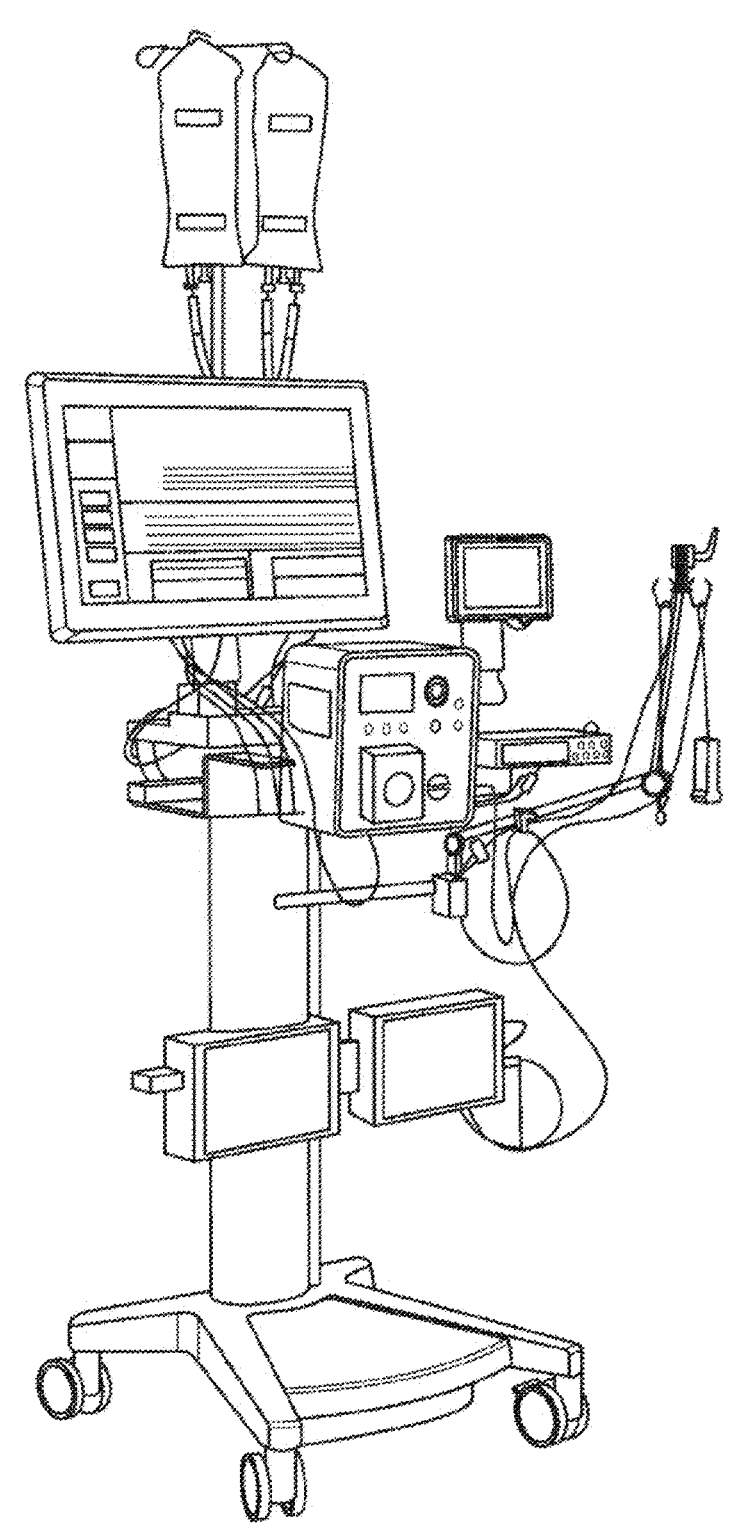
FIG. 1 illustrates an example of a modular computerized diagnostic and infusion system for coronary and other human/animal vasculature; in accordance with some embodiments of the present subject matter.

Systems and apparatus are included that are configured to determine in real time effectiveness of apparatus and methods used to unblock microvascular obstructions (MVO). Because the results are shown in real time, apparatus and methods can be quickly changed to alter treatment and more quickly unblock or improve MVO. An infusion system using the occlusion balloon blocks antegrade flow for a short time and measures vascular pressure response as an infusate is infused in stepwise fashion at increasingly higher flowrates. During antegrade flow occlusion a calculation of the real-time vascular resistance can be made using the formula $R(t)=P(t)/Qmean(t)$ where: Qmean(t): is the flow mean values generated by the infusion system; P(t): is the distal pressure response in the vessel generated from the flow infusion; and R(t): is the calculated vascular resistance using the two other known parameters. Examples of the described invention herein may be used for coronary and other human vasculature to diagnose and treat microvascular obstruction (MVO) and tissue necrosis/infarction.

The following disclosure outlines an approach and non-clinical data generated from using this approach to measure RTIVR. The data show the ability of systems/devices/methods described herein to measure RTIVR, Tau and Waterfall Pressure and that these parameters can detect MVO and tissue necrosis/infarction.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter provides devices, systems and methods for unique techniques for measuring RTIVR to diagnose and treat microvascular obstruction (MVO) and tissue necrosis/infarction. This application also incorporates by reference the entirety of the subject matter disclosed in U.S. patent application Ser. No. 15/398,470, filed Jan. 4, 2017, and published as U.S. Patent Application Pub. No. 2017/0189654 A1 published on Jul. 6, 2017 ("the '470 Application"). The apparatus and methods described in this application include but are not limited to the apparatus and methods described in the '470 Application.

FIG. 1 illustrates an example of a modular computerized diagnostic and infusion system 100 (hereinafter "infusion system") for coronary and other human/animal vasculature; in accordance with some embodiments of the present subject matter. The infusion system 100 can be a clinical ready modular system and can be configured in a mobile console form. The infusion system 100 enables MVO diagnosis by at least one or more of the following:

real-time coronary artery pressure and flow;
  pressure/resistance time parameters;
  Waterfall Pressure or Coronary Wedge Pressure;
  intracoronary electrocardiogram (ECG); and/or
  fractional flow reserve (FFR) measurements.

The infusion system 100 can enable MVO therapy by at least one or more of the following:

infusion of approved agent(s);
  targeted and low flow infusion; and/or
  continuous monitoring of diagnostic parameters.

Figure 2:
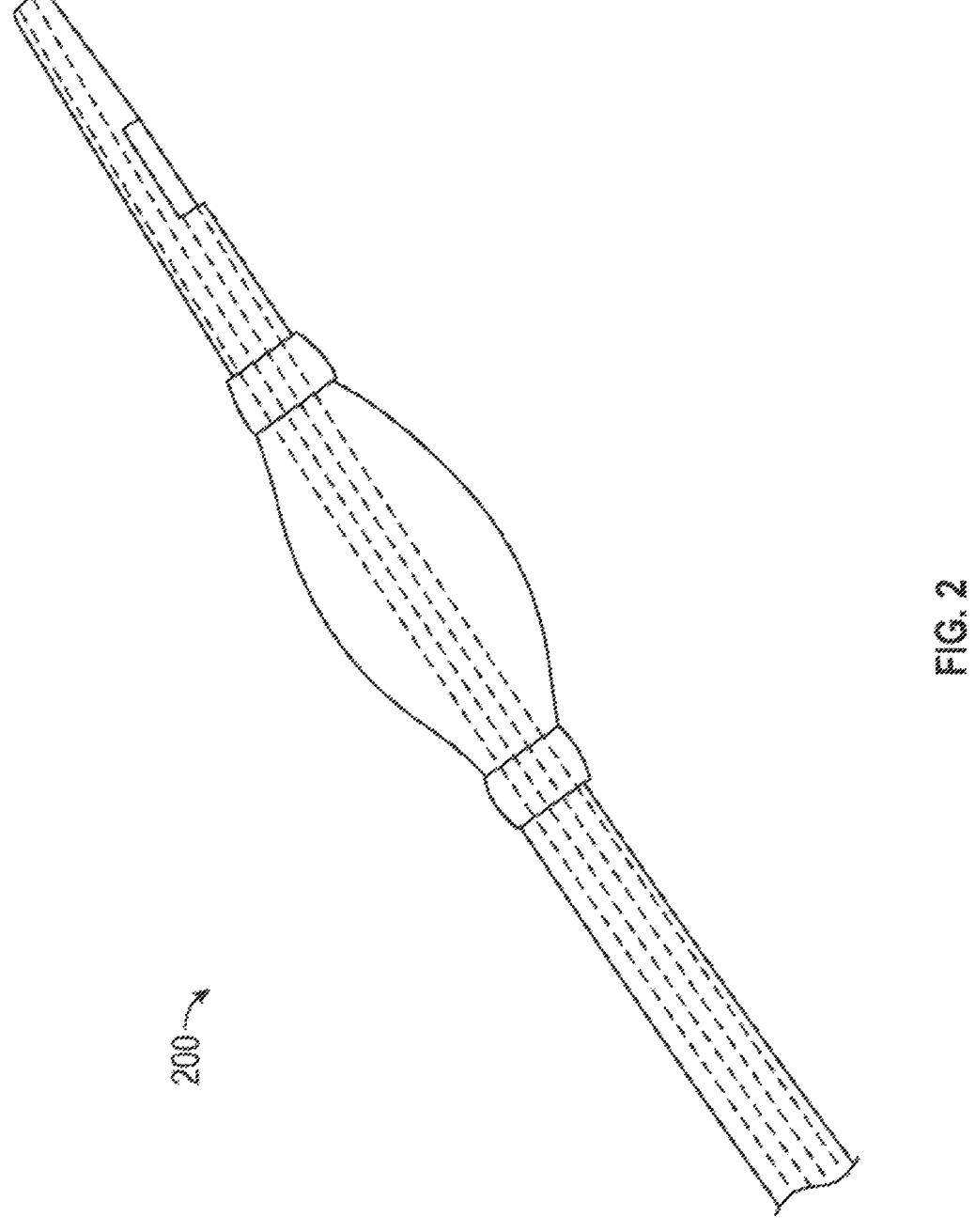
FIG. 2 illustrates an example of an infusion catheter having an occlusion balloon, in accordance with some embodiments of the present subject matter.
Figure 3:
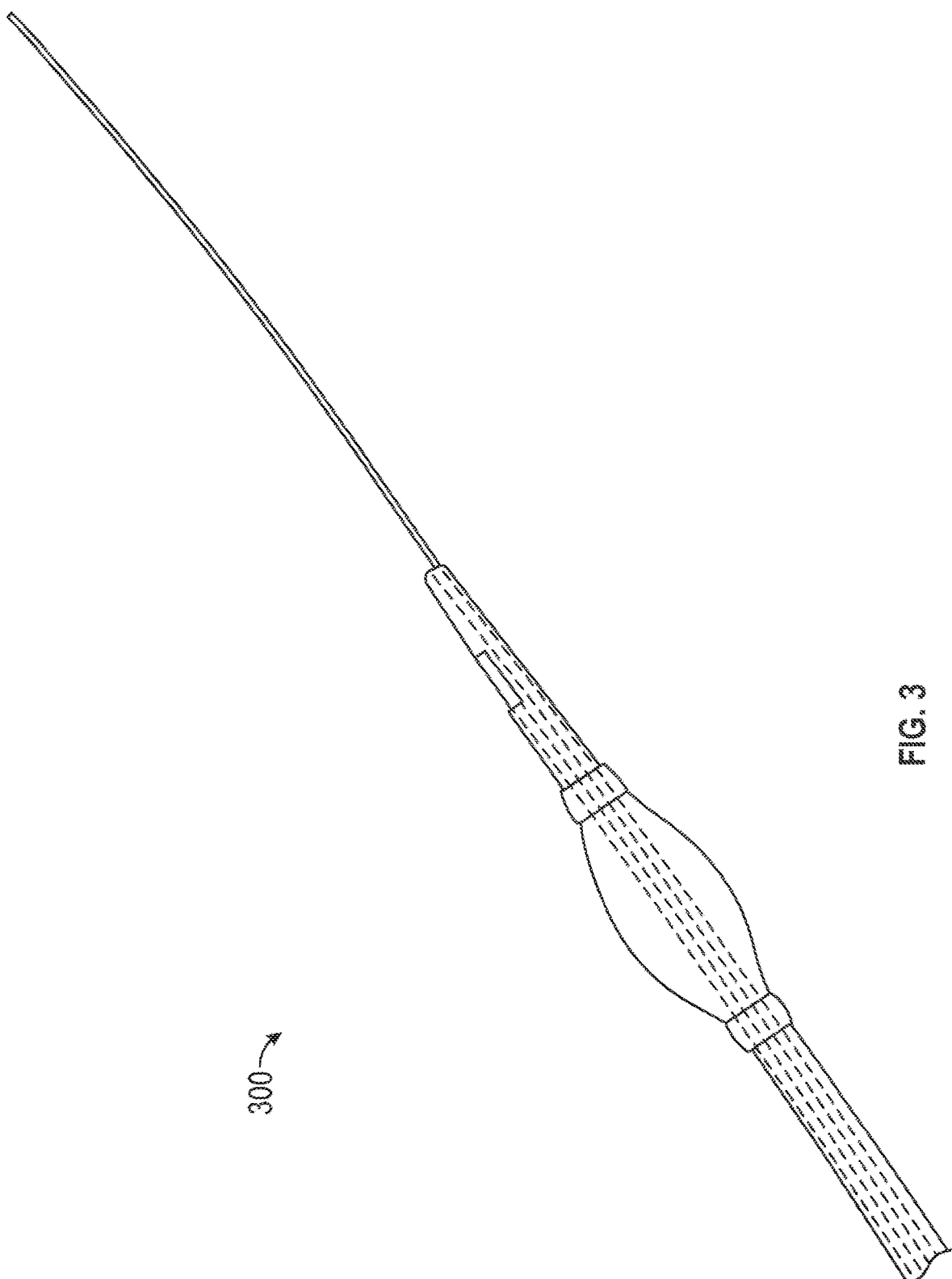
FIG. 3 illustrates an example of an infusion catheter having an occlusion balloon, in accordance with some embodiments of the present subject matter.

FIG. 2 illustrates an example 200 of an infusion catheter having an occlusion balloon, balloon markers and infusion lumen in accordance with some embodiments of the present subject matter. FIG. 3 illustrates an example 300 of an infusion catheter having an occlusion balloon placed over a 0.014" pressure measuring guide wide in a rapid-exchange (RX) fashion, in accordance with some embodiments of the present subject matter. The infusion catheters as shown in FIGS. 2-3 can be used in systems/devices/methods described herein to occlude a desired vessel, infuse desired fluids and measure pressure inside the vessel in real time and distal to the occlusion balloon. The infusion catheters as shown in FIGS. 2-3 can include: a 6F guide sheath compatible catheter, a compliant 5×10 mm occlusion balloon, and can be received over 0.014" pressure guide wire. The infusion catheters as shown in FIGS. 2-3 can include a wide flow infusion range, for example, 5-50 ml/min and can include axial flow infusion. A person of skill would appreciate that catheter dimensions, configurations, and infusion ranges may vary and remain within the scope of the present subject matter.

In some embodiments, the catheter can be inserted into a myocardial vessel supplying blood to a patient's myocardium. In some embodiments, the myocardial vessel or nearby vessels may or may not include MVO or and may or may not include myocardial infarction. The catheter can block antegrade blood flow within the myocardial vessel around the catheter by inflating a balloon. In some embodiments, the myocardial vessel can include a stent and the catheter can block antegrade blood flow from within the stent, by inflating a balloon.

Figure 4:
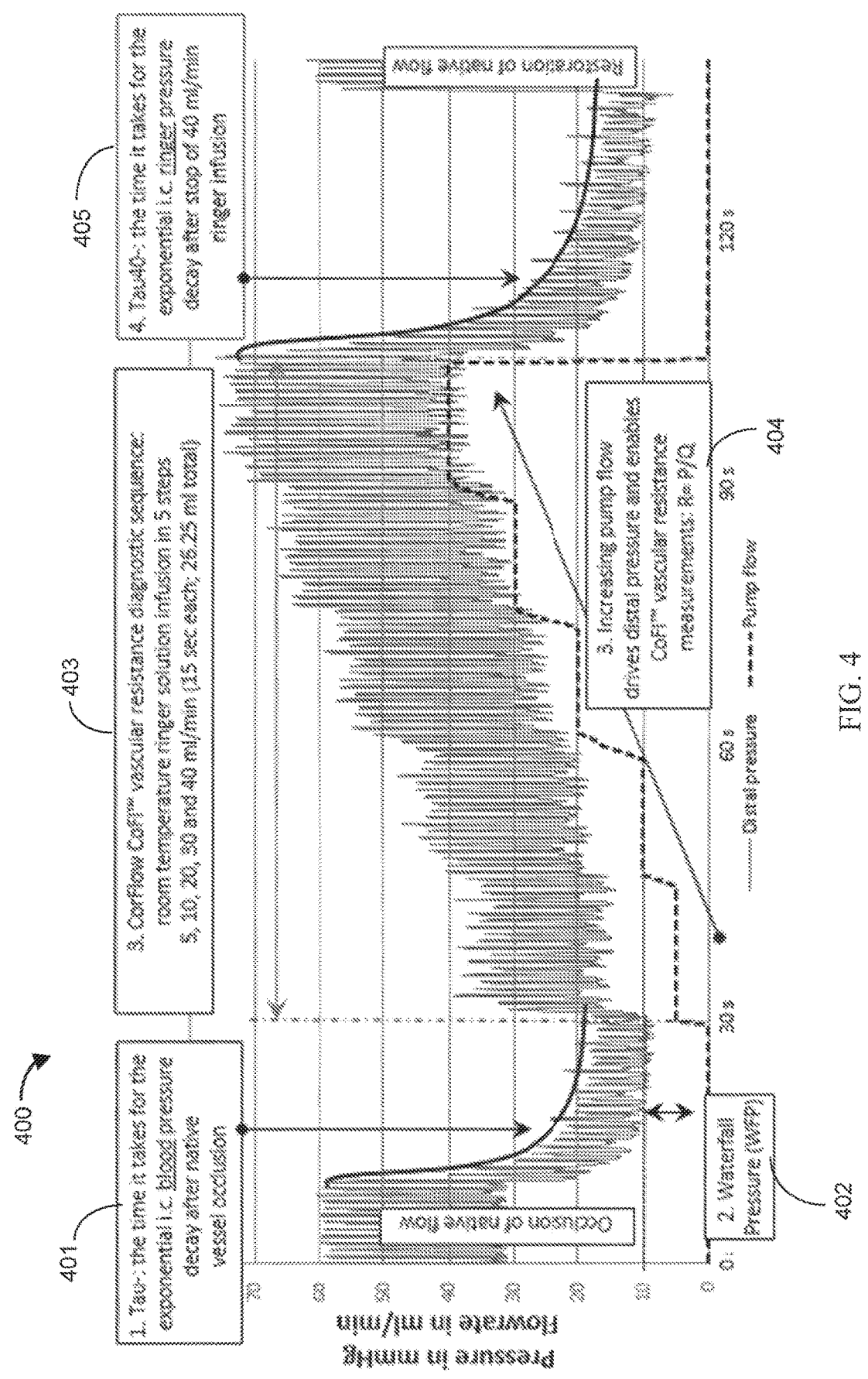
FIG. 4 illustrates a graph of an occlusion and infusion algorithm, in accordance with some embodiments of the present subject matter.

FIG. 4 illustrates a graph 400 of an occlusion and infusion algorithm, in accordance with some embodiments of the present subject matter. In some embodiments, systems/devices/methods described herein can include an infusion algorithm. The infusion algorithm can be generated by modular computerized infusion system 100 such as is shown in FIG. 1. The infusion system 100 can measure the native coronary blood pressure distal to the occlusion balloon while the vessel is not occluded. At vessel occlusion, the infusion system 100 can measures the time (Tau-) and pressure parameters for the pressure drop-off. In graph 400, the measurement of Tau- is shown at 401. The infusion system 100 can measure the waterfall pressure (WFP) or coronary wedge pressure (CWP) when these values are stable. In graph 400, the measurement of WFP is shown at 402. In some embodiments, the infusion system 100 then infuses saline or ringer solution in a step-wise fashion. In this example the flow is increased stepwise from 0 ml/min to 5, 10, 20, 30 and 40 ml/min and holds each flow value for 15 seconds. After the last flow infusion of 40 ml/min, the flow is stopped and the pressure drop off called Tau40- is measured. After the Tau40-, the WFP and CWP are measured again, the balloon is deflated and antegrade blood flow re-established. The pressures, numbers of steps, and times of infusion can be varied without changing the intention of the present disclosure. In graph 400, measurements of the stepwise pressure increases are shown at 403 and 404. In graph 400, measurement of Tau40- is shown at 405.

In some embodiments, Tau- can be described as the time it takes for the exponential intracoronary. blood pressure decay after native vessel occlusion. In some embodiments, infusion system 100 vascular resistance diagnostic sequence can include: room temperature ringer solution infusion in 5 steps, 5, 10, 20, 30 and 40 ml/min (15 sec each; 26.25 ml total). In some embodiments, increasing pump flow can drive distal pressure and enable infusion system 100 vascular resistance calculation: R=P/Q. In some embodiments, Tau40- can be described as the time it takes for the exponential intracoronary ringer pressure decay after stop of 40 ml/min ringer infusion.

Figure 5:
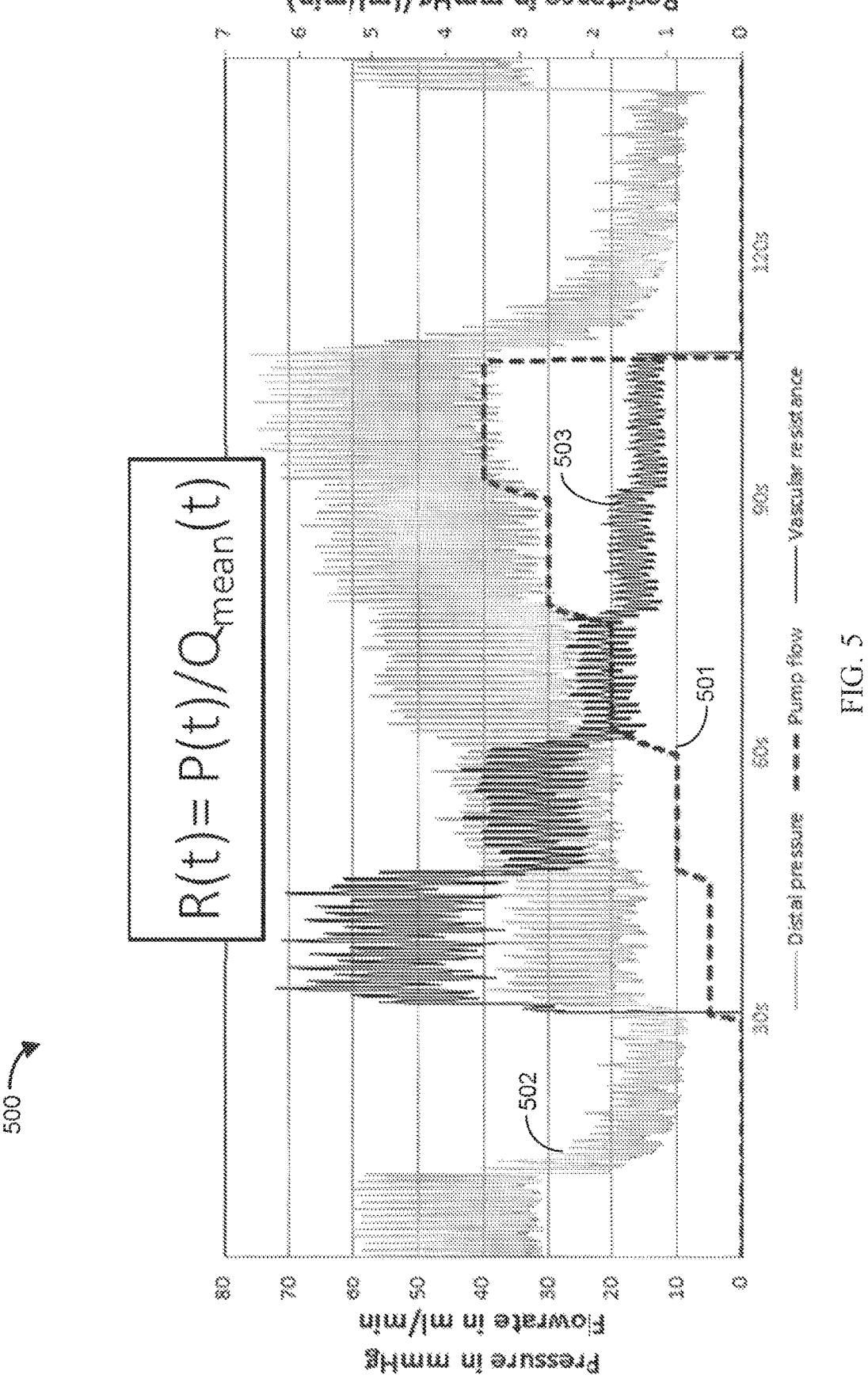
FIG. 5 illustrates a graph calculating real-time intracoronary vascular resistance, in accordance with some embodiments of the present subject matter.

FIG. 5 illustrates a graph 500 of calculating real-time intracoronary vascular resistance, in accordance with some embodiments of the present subject matter. In graph 500, measurements of pressure decay (Tau), Waterfall Pressure (WFP) or Coronary Wedge Pressure (CWP) and real-time intracoronary vascular resistance are shown. FIG. 5 shows how the real-time intracoronary vascular resistance is calculated using the infusion algorithm described below. In FIG. 5, the pump flow is a dotted line denoted as 501, the distal pressure is a lighter gray line denoted as 502 and the vascular resistance is a dark line denoted by 503. In some embodiments, systems/devices/methods described herein can include the following:

As the flow increases over the steps 0 ml/min to 5, 10, 20, 30 and 40 ml/min the infusion system 100 calculates the real-time vascular resistance using the formula $R(t)=P(t)/Q_{mean}(t)$ where:

$Q_{mean}(t)$ is the flow mean values generated by the infusion system,

P(t) is the distal pressure response in the vessel generated from the flow infusion, and R(t) is the calculated vascular resistance using the two other known parameters.

In some embodiments, systems/devices/methods described herein can provide that as the flow increases the vascular resistance drops off and the vascular resistance reaches a minimum plateau around the normal coronary flow of 30-40 ml/min. In some embodiments, systems/devices/methods described herein can provide that the largest change in the vascular resistance occurs at low flow values most likely caused by a "diode" effect as smaller flow values are not sufficient to open up the coronary microcirculation.

In some embodiments, the capacitance seen in the pressure-flow dynamics within a cardiac vessel can be related to elastance of the heart muscle itself as well as elastance of the capillary/microvasculature. In some embodiments, the capacitance can include substantial diagnostic function related to myocardial structure and fibrosis of the cardiac skeleton. In some embodiments, this function can be an important clinical implication.

FIGS. 6-31 relate to an MVO model developed using embodiments described above to measure coronary vascular resistance. In some embodiments, the MVO model can be used in an in vitro fashion or in humans or animals. In some embodiments, FIGS. 6-31 relate to a porcine non-clinical MVO model developed using embodiments described above to measure coronary vascular resistance. In some embodiments, systems/devices/methods described herein can provide a porcine occlusion-reperfusion model which generates a consistent degree of MVO as found in humans. In these non-clinical trials the MVO was 2.34±1.07% of the total left ventricle which is consistent with human findings. In some embodiments, it has been shown that the model does not generate micro-thrombi due to the use of heparin anticoagulation. In some embodiments, it has been shown that low-dose heparin experiments generate micro-thrombi. In some embodiments, it has been shown that MVO is not being generated in test subjects with high collateralization.

The present non-clinical MVO model includes systems/devices/methods described herein that provide that MVO was created in a consecutive series of 15 animals at the University of Zürich/ETH.

In an example method:

n=15 (total series n=23)

57 kg (50-74 kg) pigs

Heparinized w/ACT>150, open chest for defibrillation w/preloaded amiodarone.

90 min LAD occlusion with an infusion catheter such as shown in FIGS. 2-3 having an occlusion balloon distal to the 2nd diagonal.

All pressure measurements completed without nitrates.

Reperfusion for 6 h before gadolinium contrast enhanced MRI scan.

Measurements and imaging used:

Procedural angiograms.

Full infusion system parameters (Tau, WFP and real-time resistance) at three time points (n=7):

T1: before vessel occlusion;

T2: after 90 min occlusion and 10 min reperfusion; and

T3: after total of 4 h (240 min) of reperfusion before transport to the MRI.

Continuous pressure wire recordings using an example pressure guidewire.

Intracoronary ECG measurements over the pressure guidewire.

MRI scans: Full functional imaging; Early and late gadolinium enhanced imaging; Hi resolution imaging in perfused non-beating hearts in >5 subjects.

Histology of core infarct and border zone; detailed histology in selected subjects.

Figure 6:
FIG. 6 illustrates a photographic slide of porcine non-clinical trials showing angiographic no-reflow after a 90 minute left anterior descending artery (LAD) occlusion distal to the second diagonal, in accordance with some embodiments of the present subject matter.
Figure 7:
FIG. 7 illustrates a photographic slide of porcine non-clinical trials showing a two chamber hi-resolution gadolinium enhanced magnetic resonance imaging (MRI) scan with microvascular obstruction (MVO), in accordance with some embodiments of the present subject matter.
Figure 7:
Figure 8:
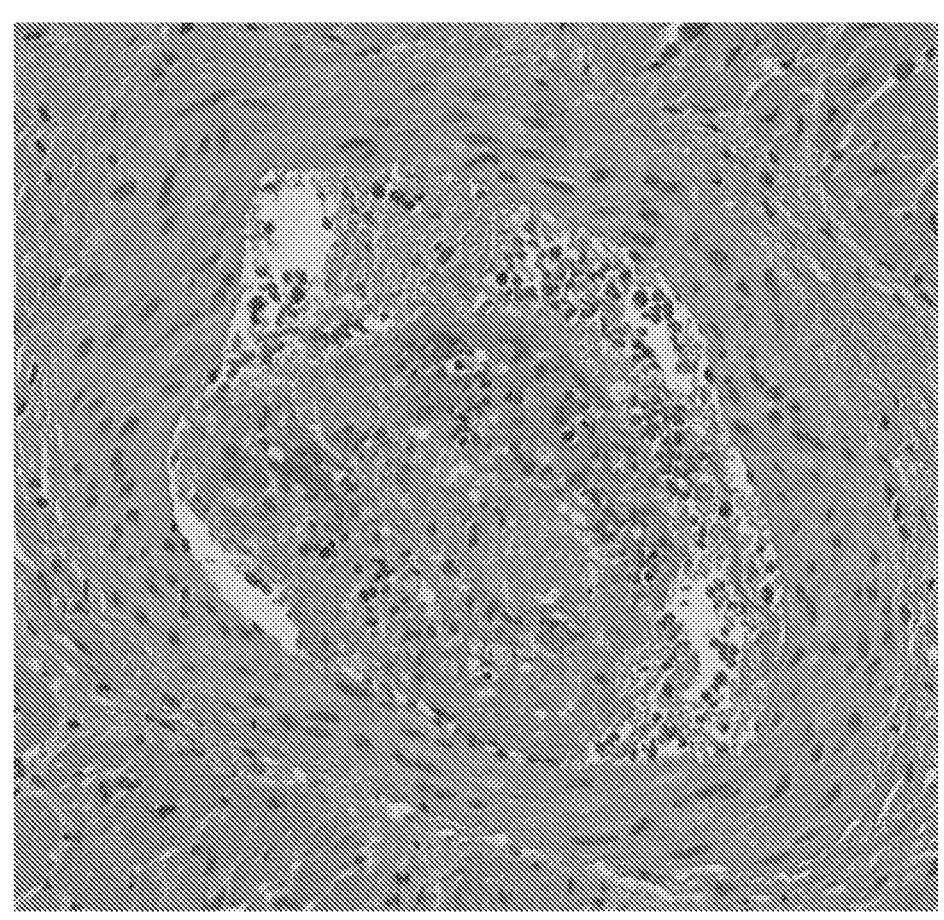
FIG. 8 illustrates a photographic slide of porcine non-clinical trials showing platelet rich MVO in a 200 micrometer vessel, in accordance with some embodiments of the present subject matter.

FIG. 6 illustrates a photographic slide 600 of porcine non-clinical trials showing angiographic no-reflow after a 90 minute left anterior descending artery (LAD) occlusion distal to the second diagonal, in accordance with some embodiments of the present subject matter. FIG. 7 illustrates a photographic slide 700 of porcine non-clinical trials showing a two chamber hi-resolution gadolinium enhanced magnetic resonance imaging (MRI) scan with microvascular obstruction (MVO), in accordance with some embodiments of the present subject matter. The MVO 702 has been circled in white. FIG. 8 illustrates a photographic slide 800 of porcine non-clinical trials showing platelet rich MVO in a 200 micrometer vessel, in accordance with some embodiments of the present subject matter.

Figure 9B:
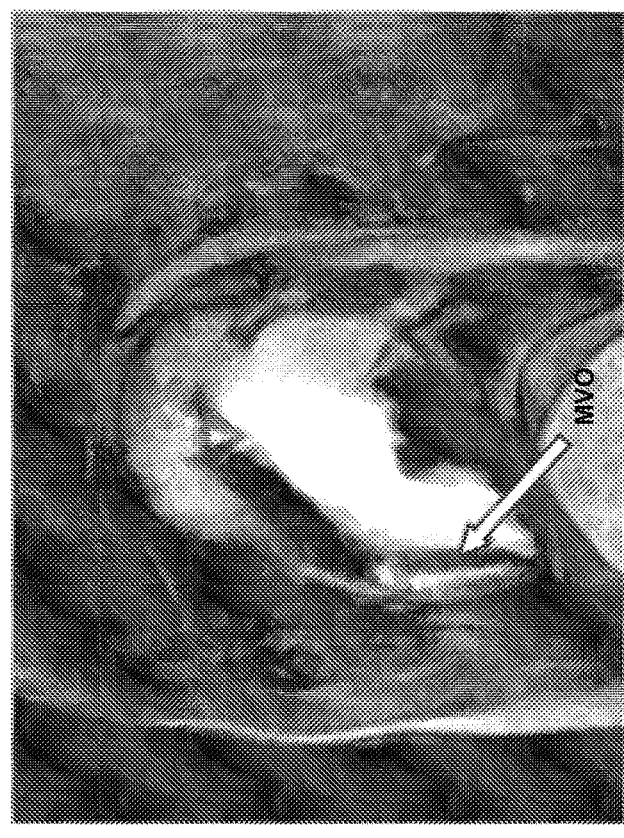
FIG. 9B illustrates a photographic slide of porcine non-clinical trials showing a two chamber magnetic resonance imaging (MRI) scan with microvascular obstruction (MVO), in accordance with some embodiments of the present subject matter.
Figure 9A:
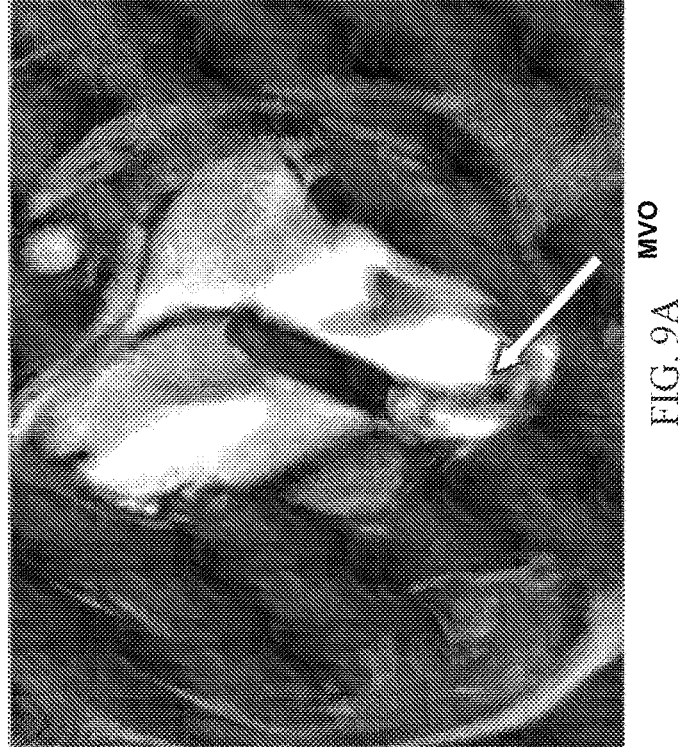
FIG. 9A illustrates a photographic slide of porcine non-clinical trials showing a four chamber magnetic resonance imaging (MRI) scan with microvascular obstruction (MVO), in accordance with some embodiments of the present subject matter.
Figure 10:
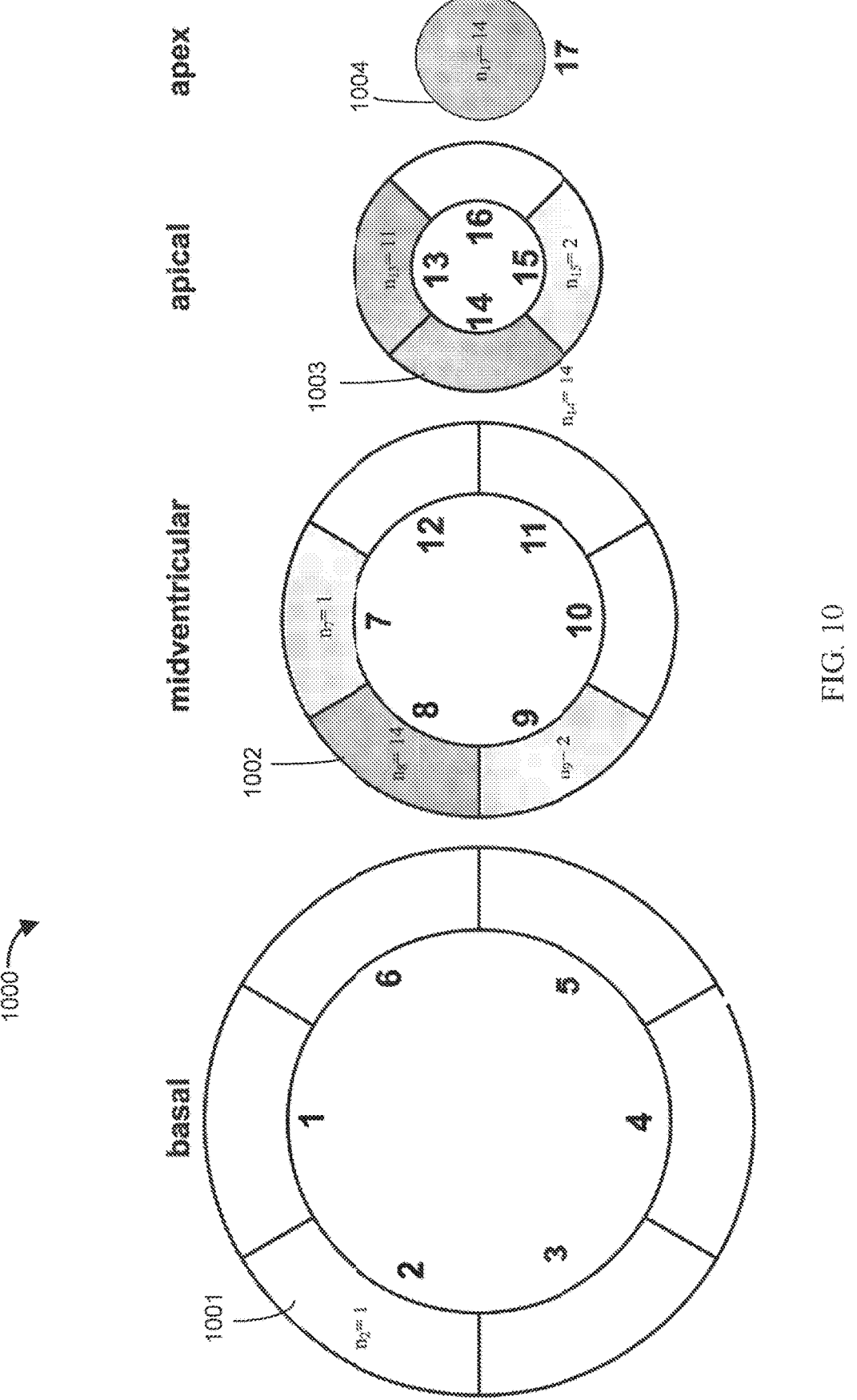
FIG. 10 illustrates a graphical representation of the MVOs location shown in FIGS. 9A-B, in accordance with some embodiments of the present subject matter.

FIG. 9A illustrates a photographic slide 900 of porcine non-clinical trials showing a four chamber magnetic resonance imaging (MRI) scan with microvascular obstruction (MVO), in accordance with some embodiments of the present subject matter. FIG. 9B illustrates a photographic slide 902 of porcine non-clinical trials showing a two chamber magnetic resonance imaging (MRI) scan with microvascular obstruction (MVO), in accordance with some embodiments of the present subject matter. In the porcine non-clinical trial MVO was generated in 14 of the 15 subjects and the MRI % MVO corresponds with human findings in large clinical trials. FIG. 10 illustrates a graphical representation 1000 of the MVOs location shown in FIGS. 9A-B, in accordance with some embodiments of the present subject matter. The graphical representation shows the MVO at the basal 1001, midventricular 1002, apical 1003, and apex 1004 positions.

Figure 11:
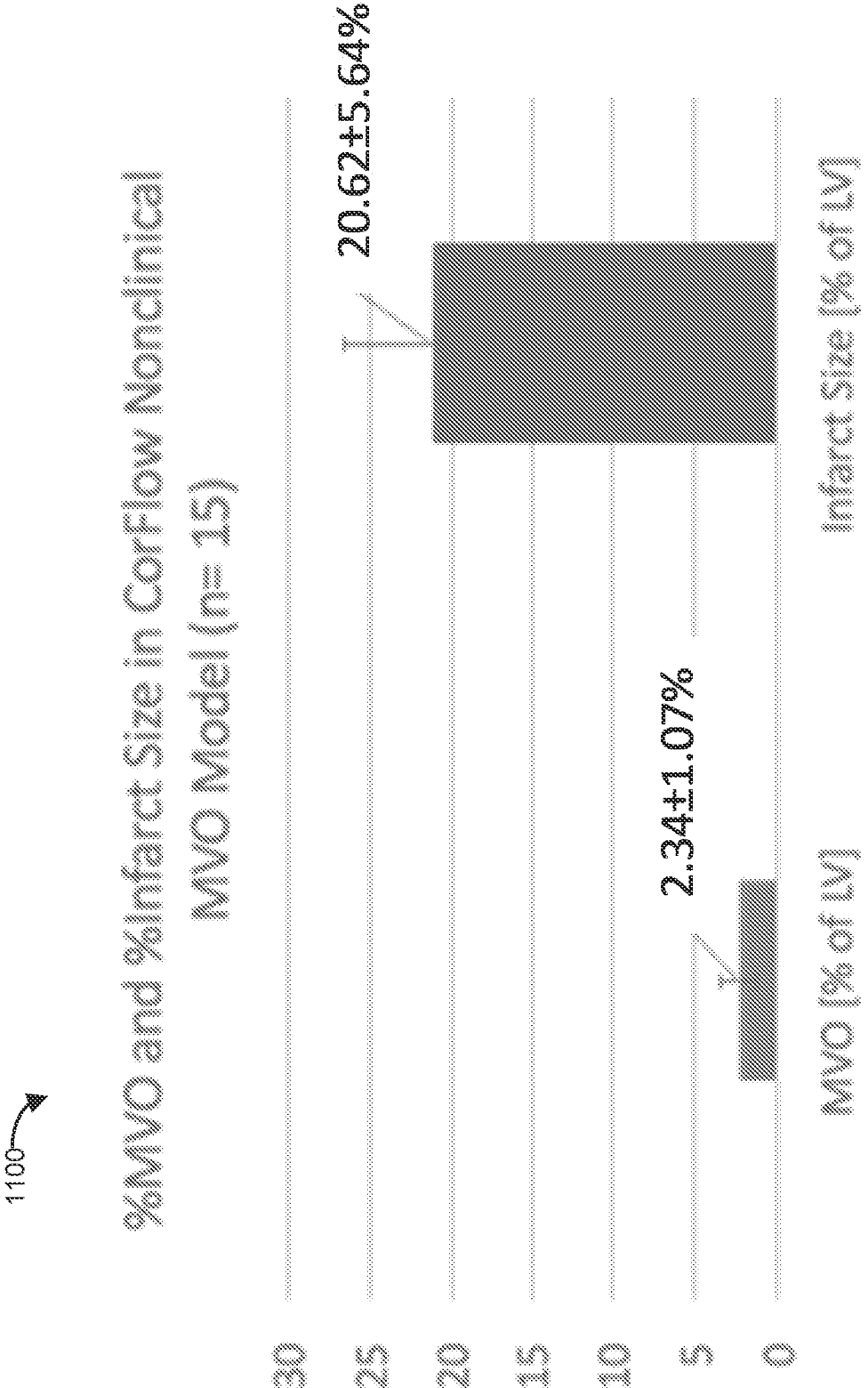
FIG. 11 illustrates a graph of porcine non-clinical trials showing a percentage of MVO and a percentage of infarct size of the total left ventricle, in accordance with some embodiments of the present subject matter.
Figure 13:
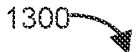
FIG. 13 illustrates a table showing results of consecutive animals in a porcine non-clinical trial to create human like MVO, in accordance with some embodiments of the present subject matter.

FIG. 11 illustrates a graph 1100 of porcine non-clinical trials showing a percentage of MVO and a percentage of infarct size of the total left ventricle, in accordance with some embodiments of the present subject matter. FIG. 12 illustrates a table 1200 comparing results of a porcine non-clinical trial to human data, in accordance with some embodiments of the present subject matter. FIG. 13 illustrates a table 1300 showing results of consecutive animals in a porcine non-clinical trial to create human like MVO, in accordance with some embodiments of the present subject matter.

Figure 14:
FIG. 14 illustrates an angiogram of a porcine non-clinical trial showing results of test subject number fourteen, in accordance with some embodiments of the present subject matter.
Figure 15:
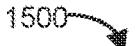
FIG. 15 illustrates an angiogram of a porcine non-clinical trial showing results of test subject number fourteen, in accordance with some embodiments of the present subject matter.

FIG. 14 illustrates an angiogram 1400 of a porcine non-clinical trial showing results of test subject number fourteen in the left anterior descending (LAD) coronary artery, in accordance with some embodiments of the present subject matter. In test subject number fourteen there was no infarct or MVO created due to substantial collateralization. FIG. 15 illustrates an angiogram 1500 of a porcine non-clinical trial showing results of test subject number fourteen at LAD with a balloon occlusion, in accordance with some embodiments of the present subject matter.

Figure 16:
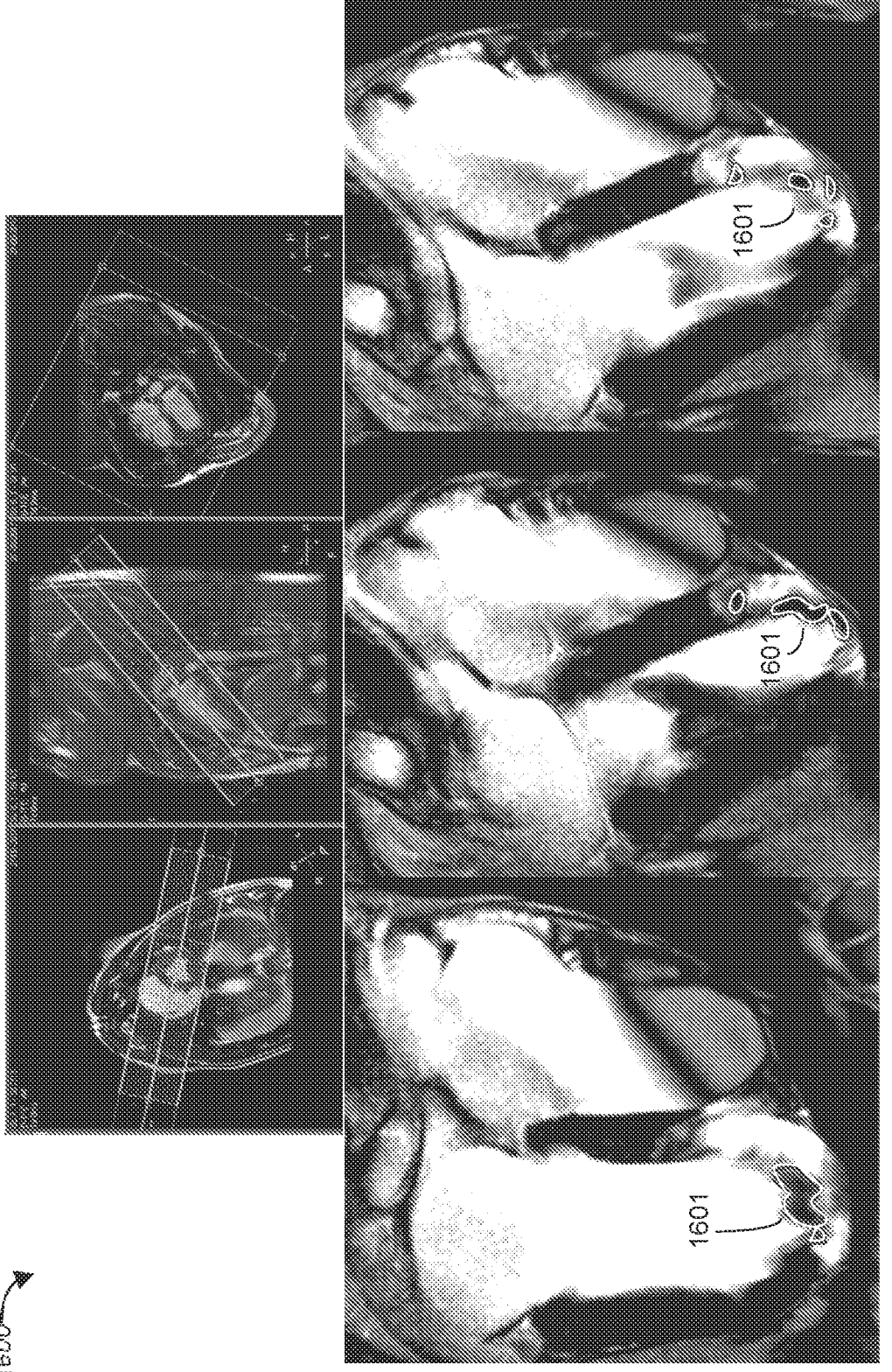
FIG. 16 illustrates data from MRI hi-resolution scans of a porcine non-clinical trial, in accordance with some embodiments of the present subject matter.

FIG. 16 illustrates data 1600 from MRI hi-resolution scans of a porcine non-clinical trial, in accordance with some embodiments of the present subject matter. Pertinent MVO information is circled in white at 1601.

Figure 17:
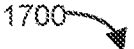
FIG. 17 illustrates position of histology sectioning blocks from the endocardial to epicardial border from section 1 of test subject 12 as shown in photographic slides in FIGS. 18-20 of a porcine non-clinical trial, in accordance with some embodiments of the present subject matter.
Figure 18:
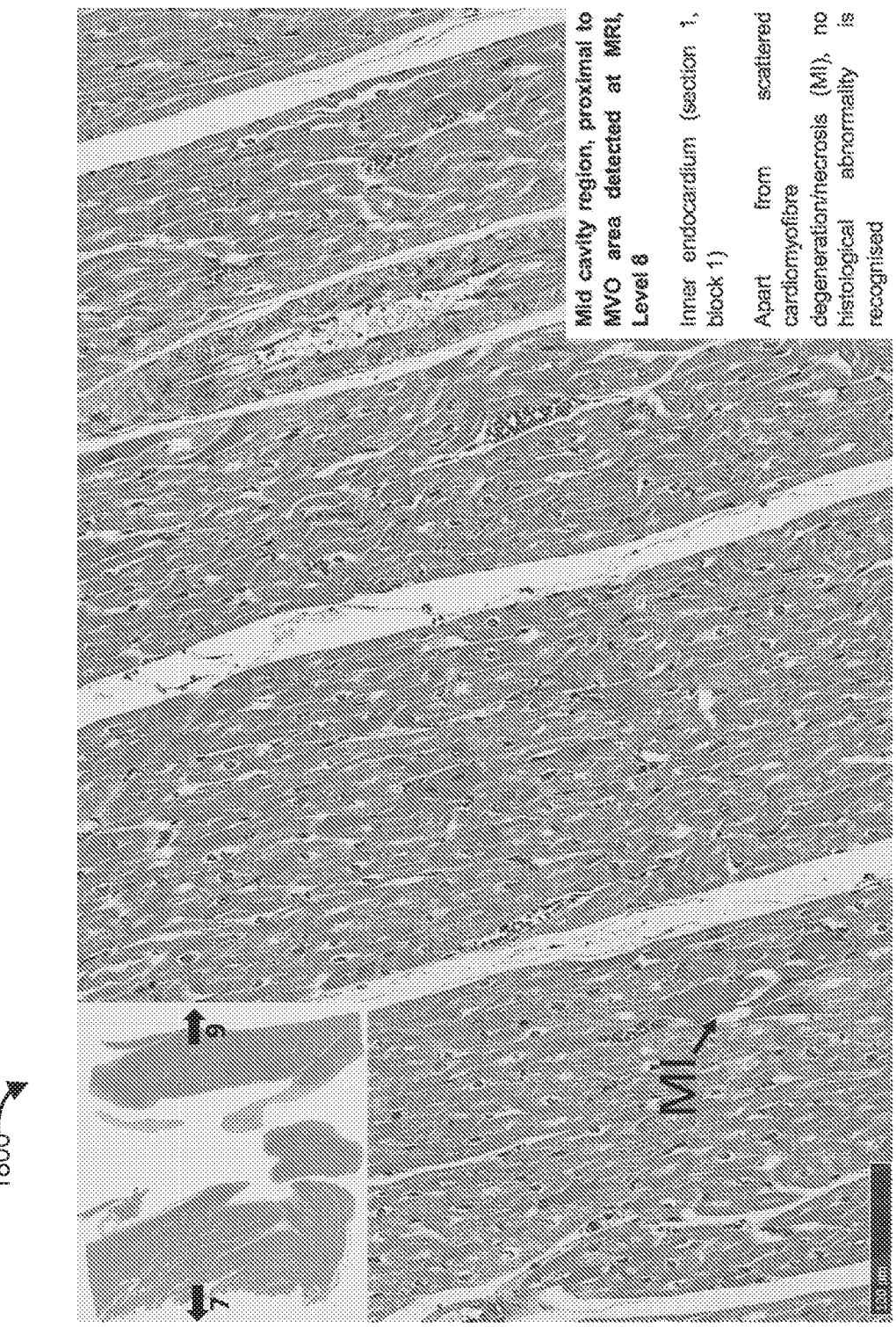
FIG. 18 illustrates a photographic slide of histology section 1, block 1 of a porcine non-clinical trial, in accordance with some embodiments of the present subject matter.
Figure 19:
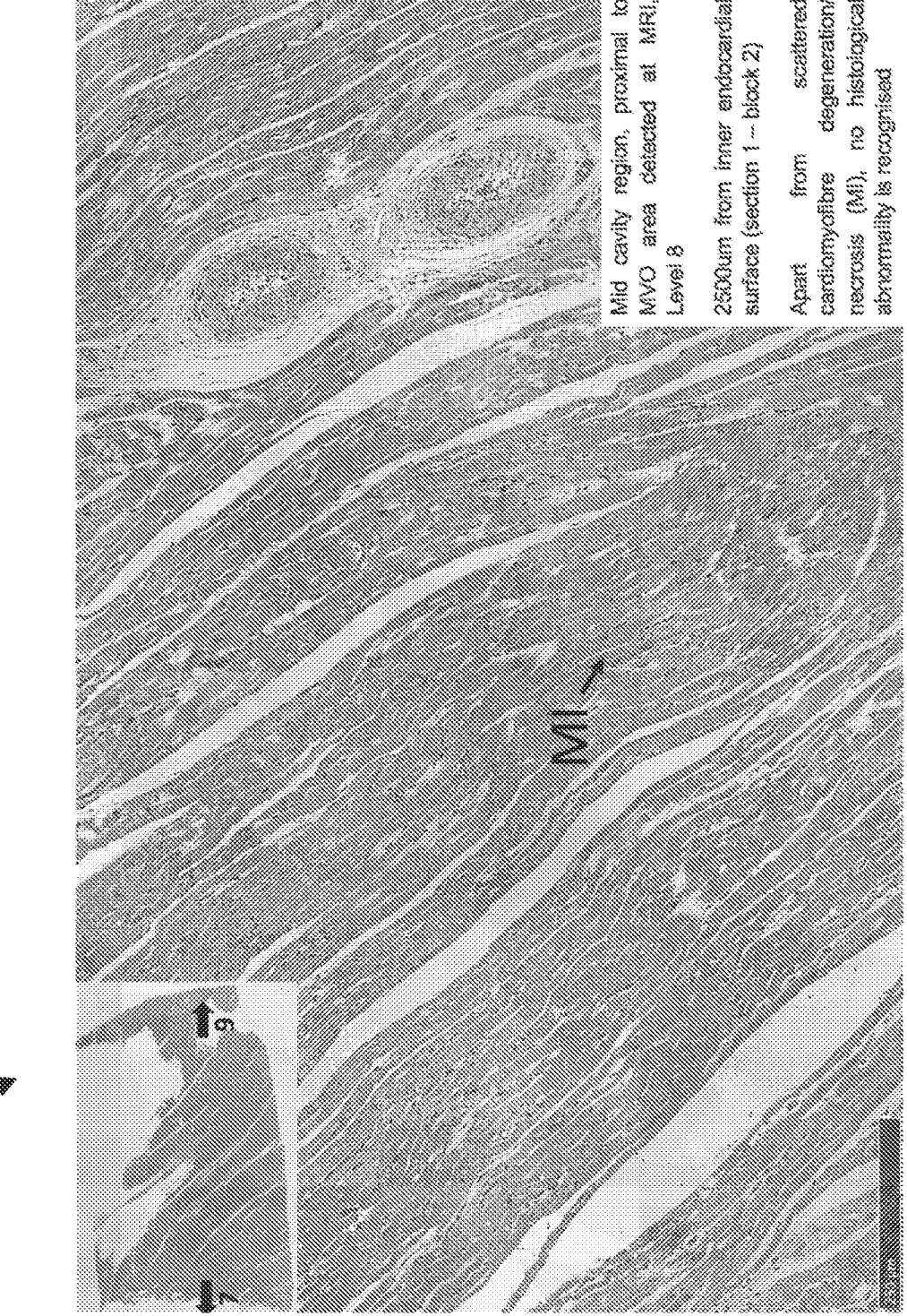
FIG. 19 illustrates a photographic slide of histology section 1, block 2 of a porcine non-clinical trial, in accordance with some embodiments of the present subject matter.
Figure 20:
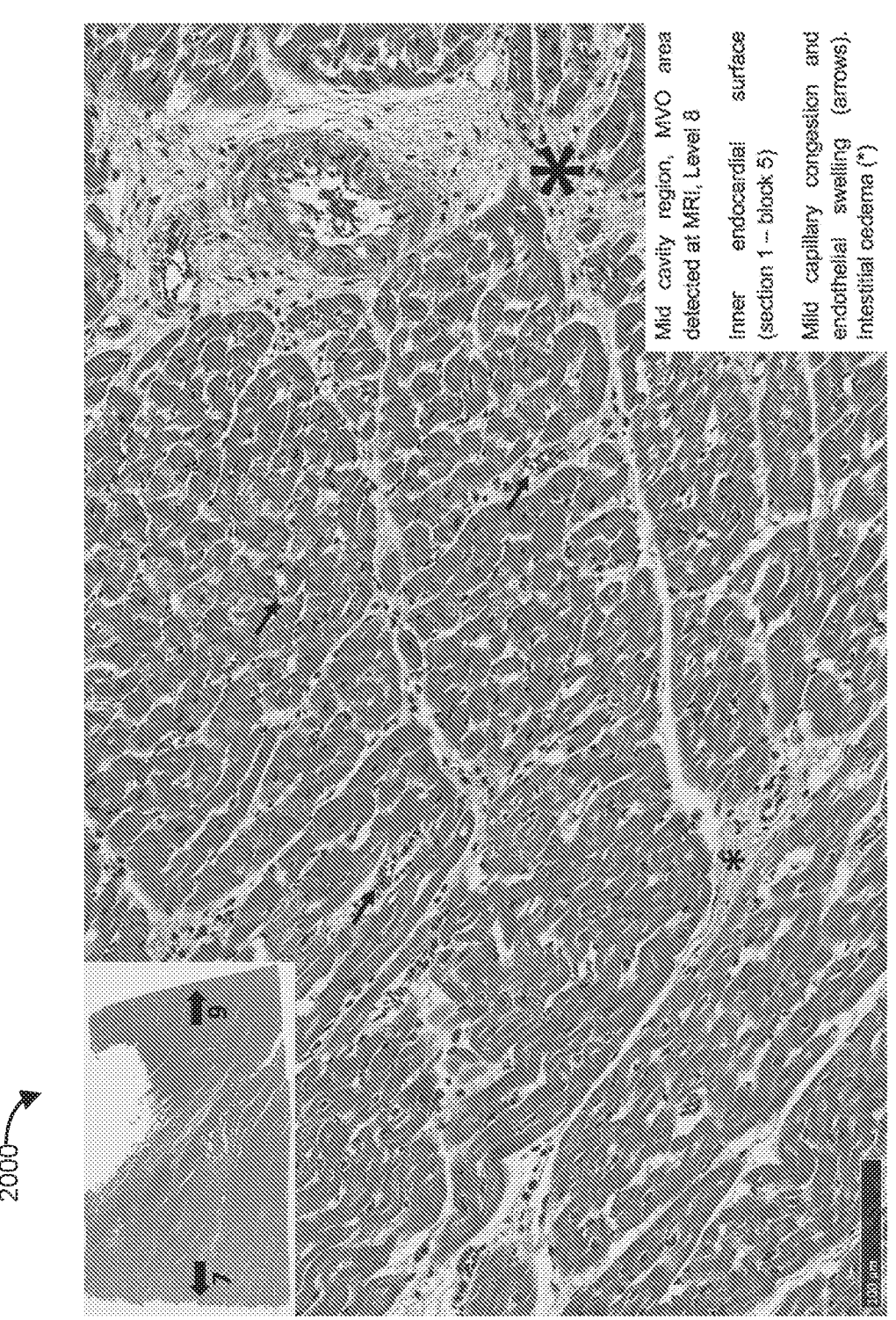
FIG. 20 illustrates a photographic slide of histology section 1, block 5 of a porcine non-clinical trial, in accordance with some embodiments of the present subject matter.

FIG. 17 illustrates position 1700 of histology sectioning blocks from the endocardial to epicardial border from section 1 of test subject 12 as shown in photographic slides in FIGS. 18-20 of a porcine non-clinical trial, in accordance with some embodiments of the present subject matter. In summary, the sectioning slides show the region immediately proximal to MVO: minimal histological changes (scattered degenerated myofibres) and no evidence of thrombosis. MVO region: Minimal to moderate myocardial degeneration/necrosis with capillary congestion and endothelial swelling. No evidence of thrombosis. As shown in FIG. 17, From each block: a) first section from inner endocardial to epicardial surface; b) blank section every 50 µm; and c) stained section every 500 µm.

FIG. 18 illustrates a photographic slide 1800 of histology section 1, block 1 of a porcine non-clinical trial, in accordance with some embodiments of the present subject matter. FIG. 18 shows the mid-cavity region proximal to MVO area detected at MVO level 8. It is located at the inner endocardium (section 1, block 1) and apart from scattered cardiomyofibre degeneration/necrosis (MI), no histological abnormality is recognized.

FIG. 19 illustrates a photographic slide 1900 of histology section 1, block 2 of a porcine non-clinical trial, in accordance with some embodiments of the present subject matter. FIG. 19 shows the mid-cavity region proximal to MVO area detected at MVO level 8. It is located 2500 micrometers from inner endocardial surface (section 1, block 2) and apart from scattered cardiomyofibre degeneration/necrosis (MI), no histological abnormality is recognized.

FIG. 20 illustrates a photographic slide 2000 of histology section 1, block 5 of a porcine non-clinical trial, in accordance with some embodiments of the present subject matter. FIG. 20 shows the mid-cavity region proximal to MVO area detected at MVO level 8. It is located at the inner endocardial surface (section 1, block 5) and apart from scattered cardiomyofibre degeneration/necrosis (MI), no histological abnormality is recognized.

Figure 21:
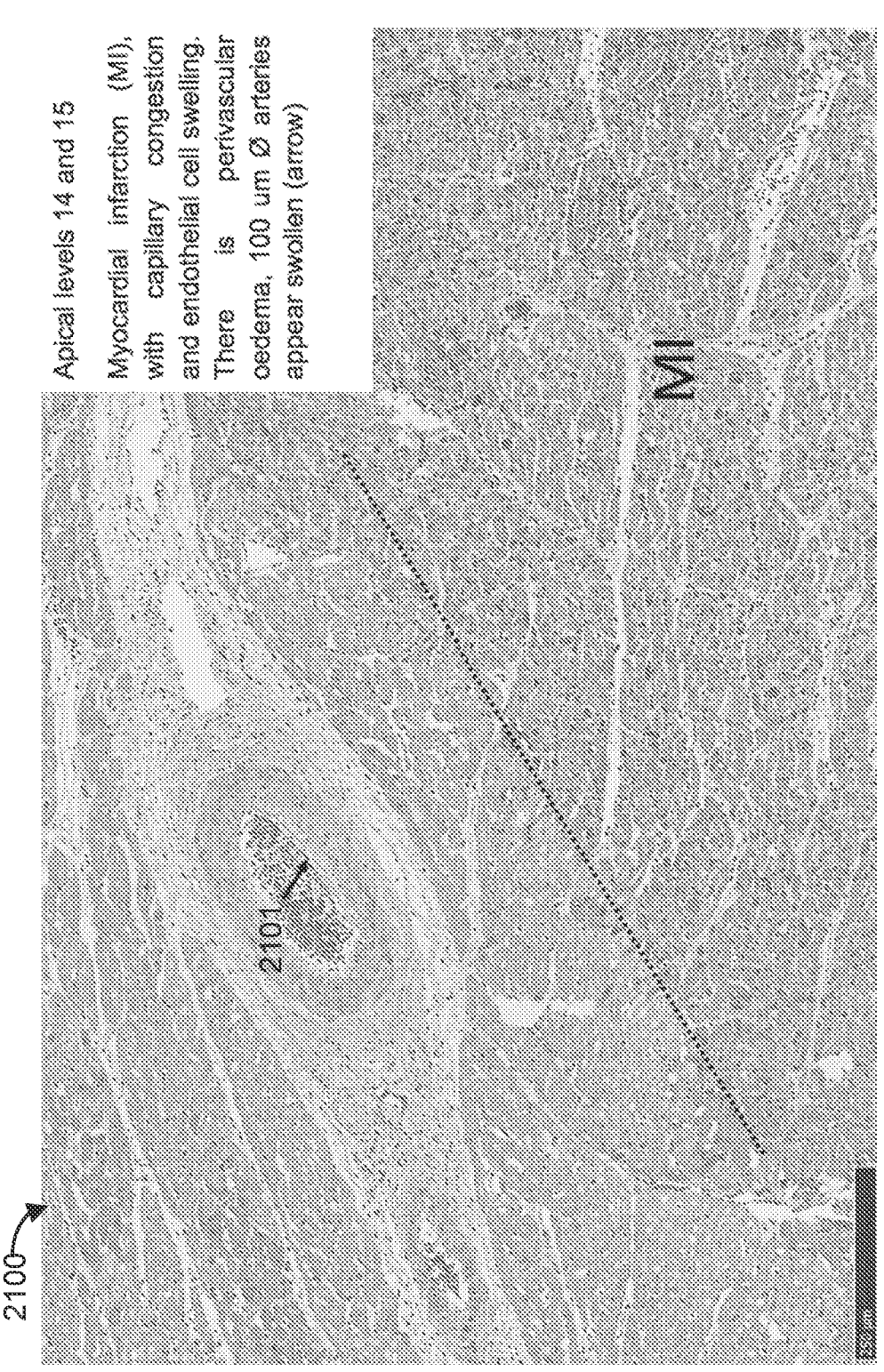
FIG. 21 illustrates a photographic slide of a histology section block 8 from test subject 8 of a porcine non-clinical trial, in accordance with some embodiments of the present subject matter.

FIG. 21 illustrates a photographic slide 2100 of a histology section block 8 from test subject 8 of a porcine non-clinical trial, in accordance with some embodiments of the present subject matter. FIG. 21 is located at apical levels 14 and 15. A myocardial infarction (MI) is shown with capillary congestion and endothelial swelling. There is perivascular oedema, 100 micrometer Ø arteries appear swollen at 2101.

Figure 22:
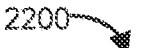
FIG. 22 illustrates a photographic slide of a histology section block 8 from test subject 3 of a porcine non-clinical trial, in accordance with some embodiments of the present subject matter.

FIG. 22 illustrates a photographic slide 2200 of a histology section block 8 from test subject 3 of a porcine non-clinical trial, in accordance with some embodiments of the present subject matter. FIG. 22 is block 8 level 14 apical region and shows thrombus at 2201 and 2202. The potential cause: plugging of microvessel with platelet rich thrombi formed in microvessel due to low dose heparin used in subject 3.

Figure 23A:
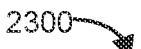
FIG. 23A illustrates a photographic slide of a histology section block 8 from test subject 3 of a porcine non-clinical trial, in accordance with some embodiments of the present subject matter.
Figure 23B:
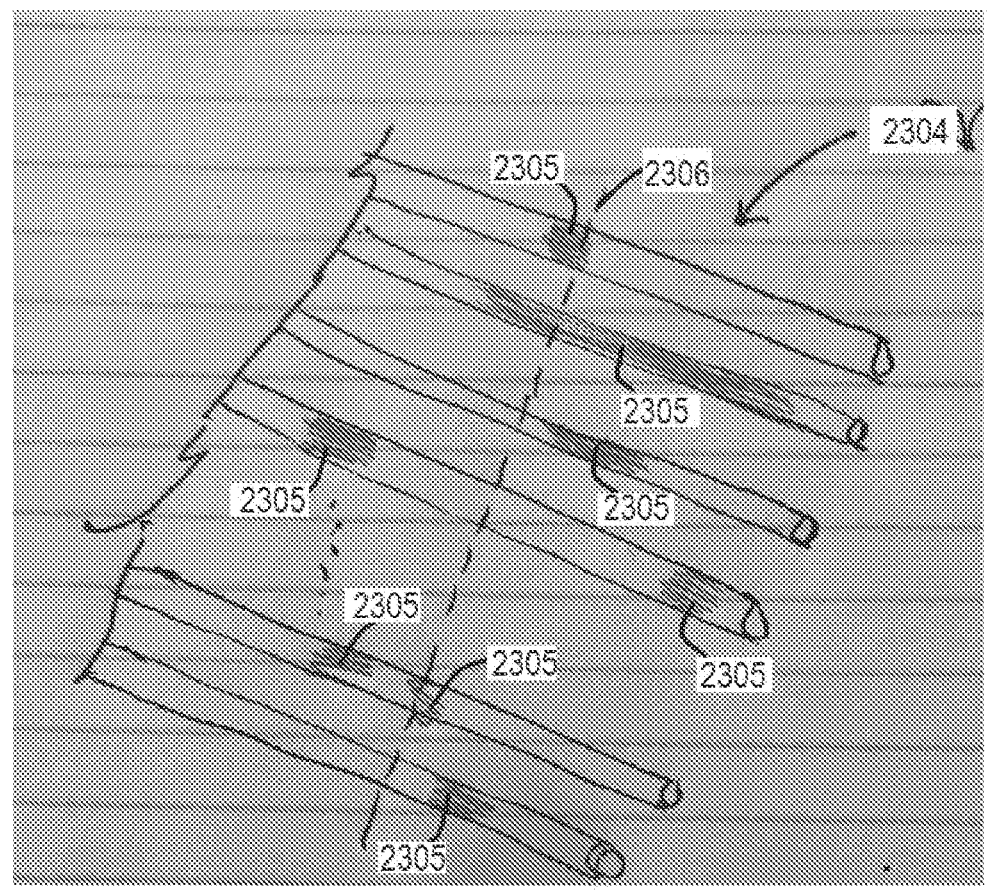
FIG. 23B illustrates an example of the MVO occurrence illustrated in FIG. 22 and FIG. 23A, in accordance with some embodiments of the present subject matter.

FIG. 23A illustrates a photographic slide 2300 of a histology section block 8 from test subject 3 of a porcine non-clinical trial, in accordance with some embodiments of the present subject matter. FIG. 23A is block 8 level 14 apical region and 200 micrometers further than FIG. 22 and shows thrombus is no longer present at each of 2301 and 2302, which correspond to thrombus locations 2201 and 2202 in FIG. 22, respectively. FIG. 23B illustrates an example of the MVO occurrence illustrated in FIG. 22 and FIG. 23A, in accordance with some embodiments of the present subject matter. FIG. 23B shows how photomicrograph slicing at different locations of multiple microvessels 2304 can indicate thrombi 2305 blockage or lack thereof depending on the slice position 2306. Pathology specimens in areas of known myocardial infarction do not show homogeneous thrombotic occlusion. Thrombus as visualized is patchy across discrete individual capillaries. A likely explanation is that thrombi are often smaller, and do not fill an entire capillary. As thrombi occur at disparate locations in vessels, a single, randomly cut histologic planar section will not intersect thrombus in each vessel. Hence, as illustrated in FIG. 23B, vessels that overall have near-total occlusion do not appear as such in a photographic slide because the histologic plane 2306 does not intersect all thrombi. For example, FIG. 22 shows the two thrombi, but FIG. 23A at 200 micrometers further shows the thrombi no longer present. This exemplifies that the microthrombi formation caused by endothelial damage can be "plug-like" platelet rich clots which do not extend along a long section of the vessel. This opens for therapeutic approaches using platelet dissolving agents which effectively can remove these smaller platelet plugs.

Figure 24:
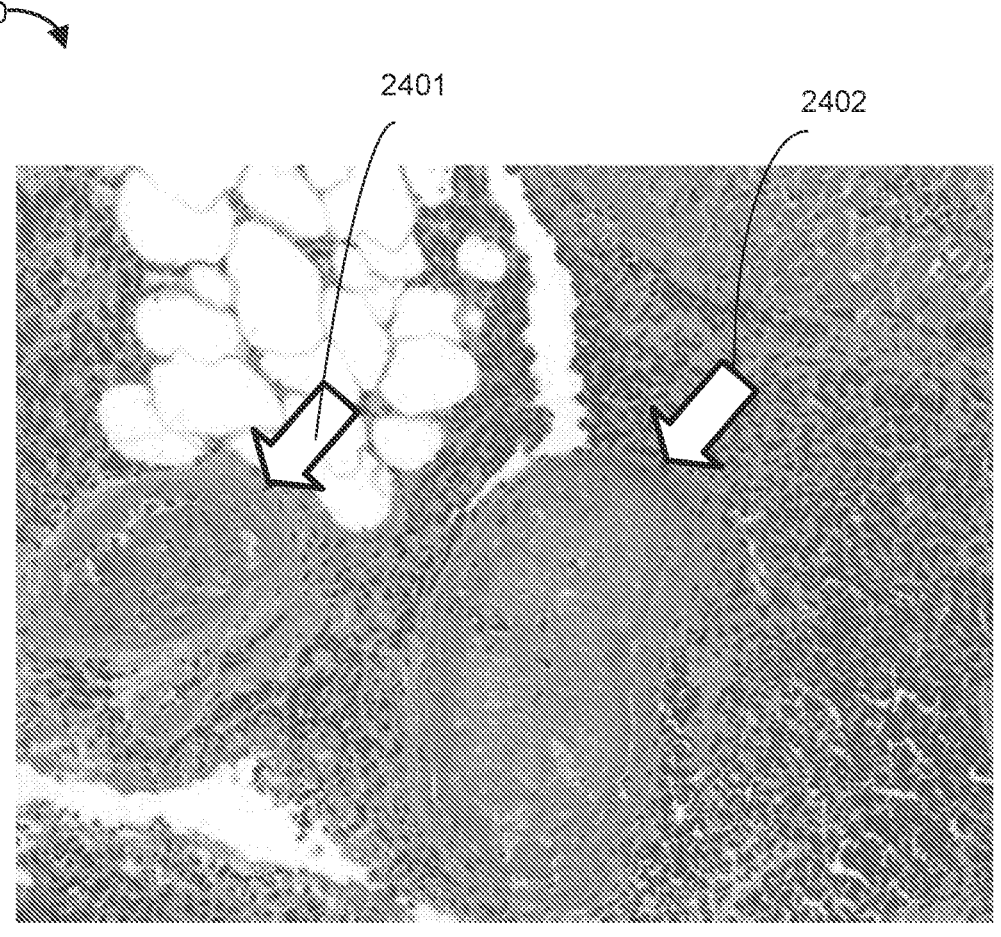
FIG. 24 illustrates a photographic slide of a human histology section, in accordance with some embodiments of the present subject matter.

FIG. 24 illustrates a photographic slide 2400 of a human histology section, in accordance with some embodiments of the present subject matter. FIG. 24 is a photomicrograph of postmortem specimen in the region of infarct. Arrows 2401 and 2402 point towards two small blood vessels completely obstructed from platelet fibrin thrombus. This microscopic examination confirms microvascular obstruction as predicted by a CMRI scan.

FIGS. 4, 5, and 25-31 document results using an example of the RTIVR Algorithm and MVO model. Embodiments of the present subject matter can include one or more of:

That the Tau- is reduced by higher degree of damage (T1, T2 and T3).

That there is a large standard deviation (SDEV) in the Tau- as it is affected by manual balloon inflation time, vessel size, native coronary blood flow etc.

That the Tau40- has a lower SDEV as it is controlled by the infusion pump and may be stopped at defined time-points also timed to the heart beats (e.g. systolic or diastolic phase of the heart beating function).

That adjusting the Tau- value for heart beats, called Tau*, creates a reliable parameter to diagnose the increased damage of the myocardium.

That Tau40*- seems to be the most accurate parameter which correlates with MVO and the infarct.

That the WFP and CWP seem unchanged throughout the experiments.

However, tau is linearly dependent on CWP.

That the Coronary Vascular Resistance mean value drops off to a plateau with increased flow as described earlier.

That the increase in the distal pressure is inversely proportional to the Coronary Vascular resistance and that this distal pressure increase also may be used to diagnose the coronary vasculature as the ringer flow infusion is made in distinct steps with defined flow values 5, 10, 20, 30 and 40 ml/min.

That there is a differentiation between RTIVR at T1, T2 and T3.

That there is a statistical significant difference in RTIVR in 7 animals.

That this statistical significant difference may be used to diagnose MVO/infarct size and to measure the effect of different treatments of the coronary vasculature in real-time while the patient is still in the catheter laboratory.

Figure 25:
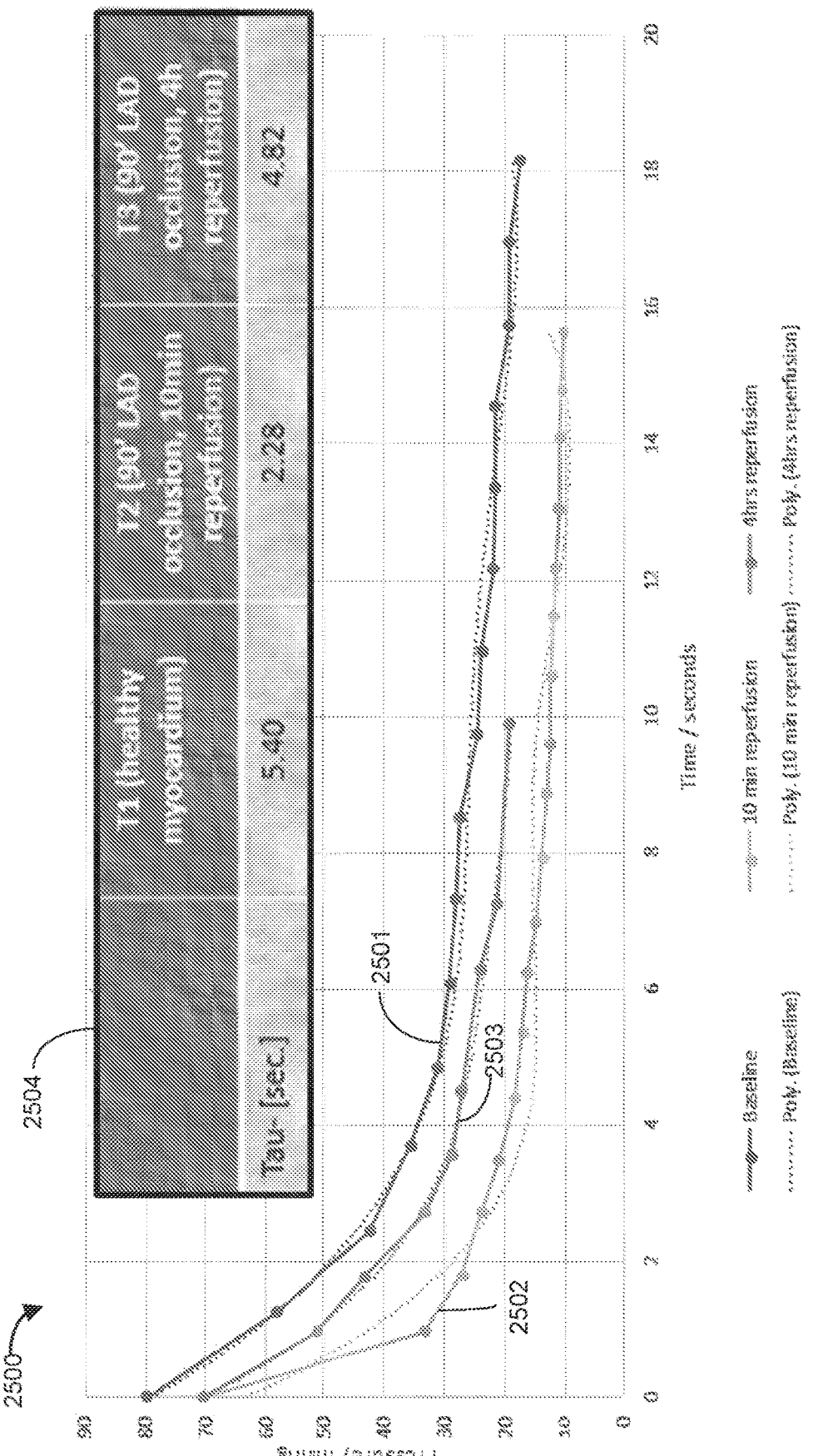
FIG. 25 illustrates a graph showing faster pressure drops in infarcted myocardium due to loss of capacitance produced with data from a porcine non-clinical trial, in accordance with some embodiments of the present subject matter.

FIG. 25 illustrates a graph 2500 showing faster pressure drops in infarcted myocardium due to loss of capacitance produced with data from a porcine non-clinical trial, in accordance with some embodiments of the present subject matter. The graph 2500 shows a baseline 2501, a 10 minute reperfusion line 2502, and a four hour reperfusion line 2503. Graph 2500 also includes a chart 2504 that shows Tau- times for T1: a healthy myocardium relating to the baseline 2501; for T2: a 90 minutes LAD occlusion relating to the 10 minute reperfusion line 2502; and for T3: a 90 minutes LAD occlusion relating to the 4 hour reperfusion line 2503. The graph 2500 also includes dotted polynomial trend lines associated with each data point line.

Figure 26A:
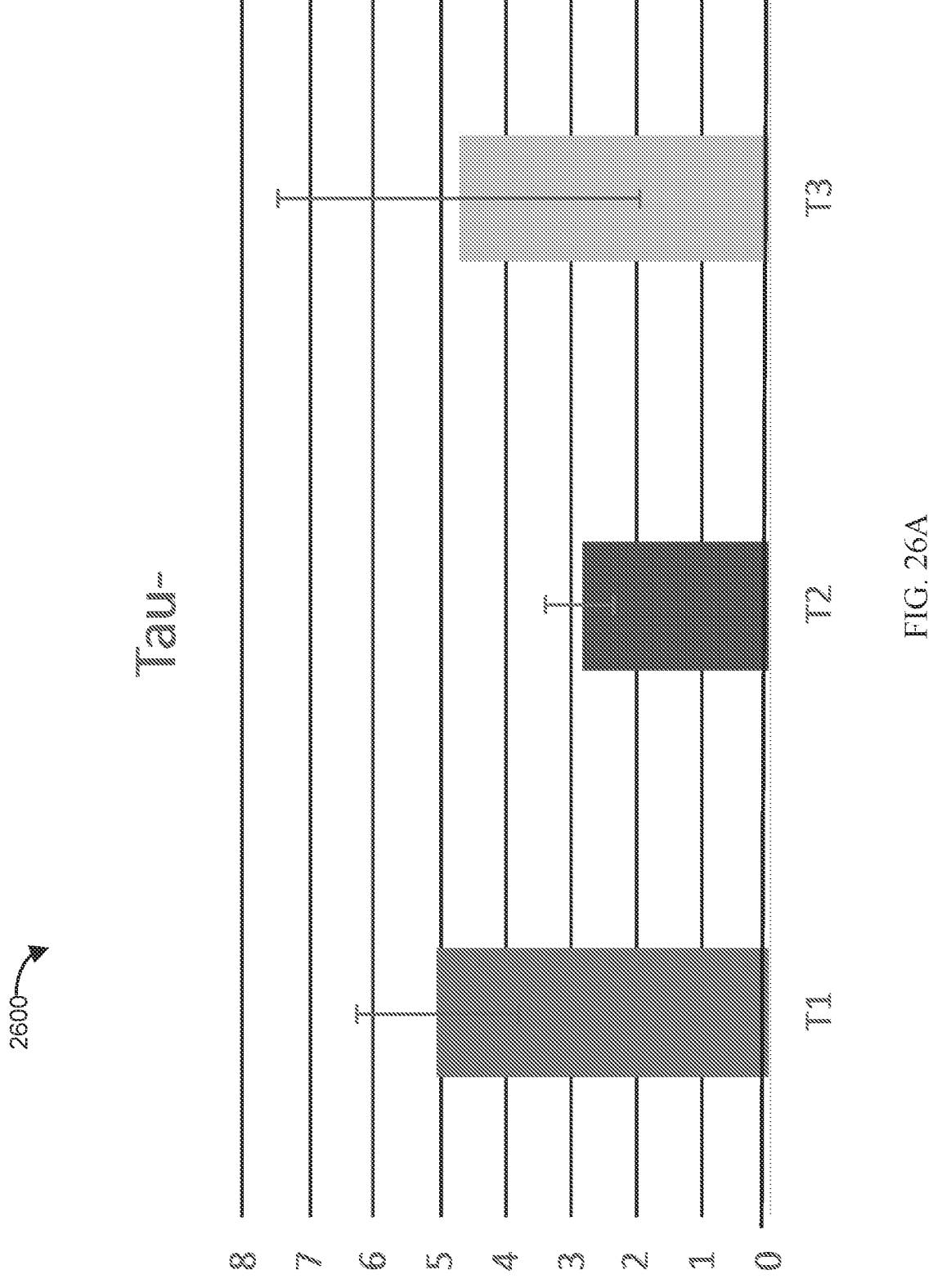
FIGS. 26A-B illustrate charts comparing Tau and Tau40 calculations without heart rate compensation from a porcine non-clinical trial, in accordance with some embodiments of the present subject matter.
Figure 26B:
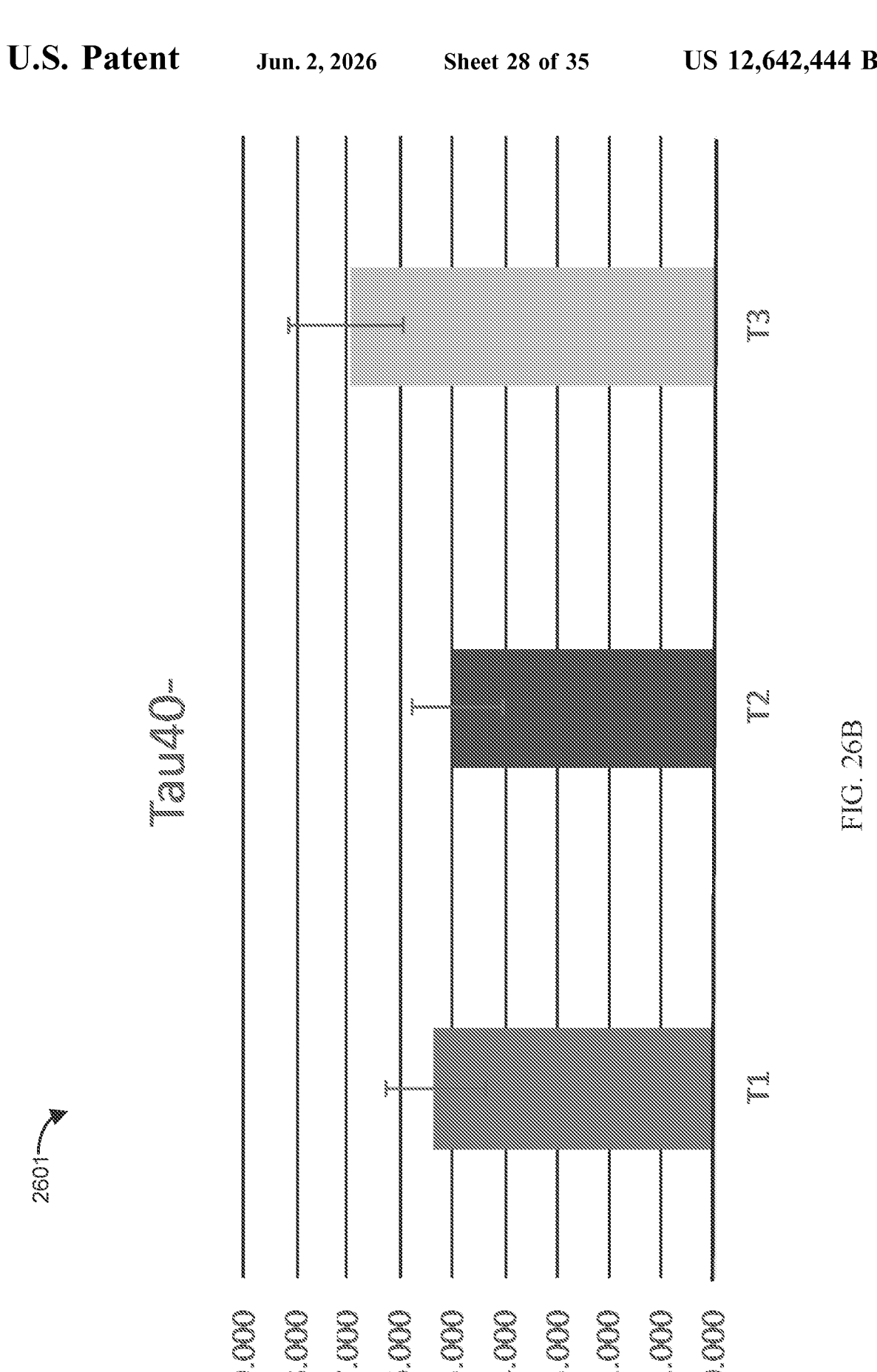
Figure 27A:
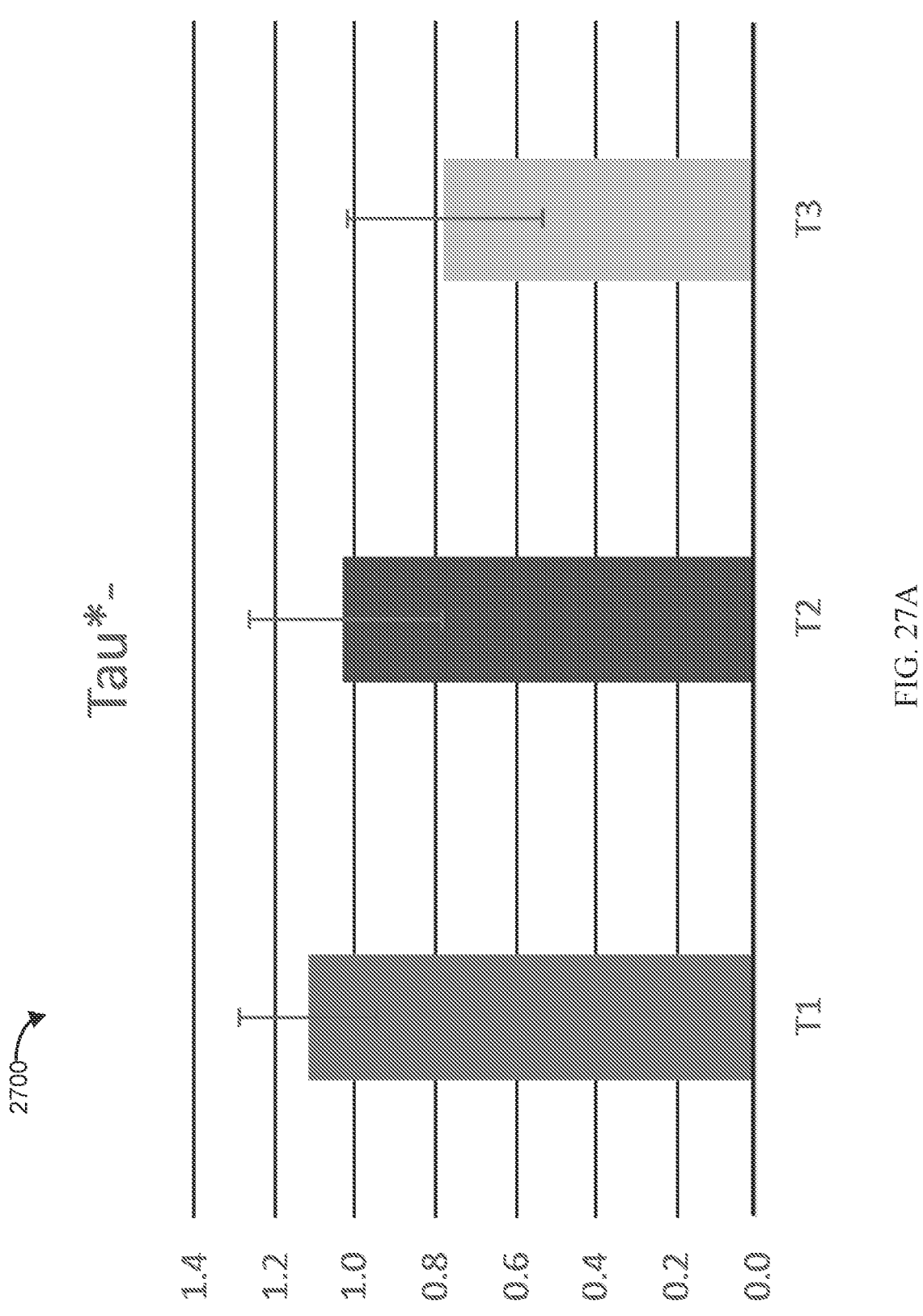
FIGS. 27A-B illustrate charts comparing Tau* and Tau40* calculations with heart rate compensation from a porcine non-clinical trial, in accordance with some embodiments of the present subject matter.
Figure 27B:
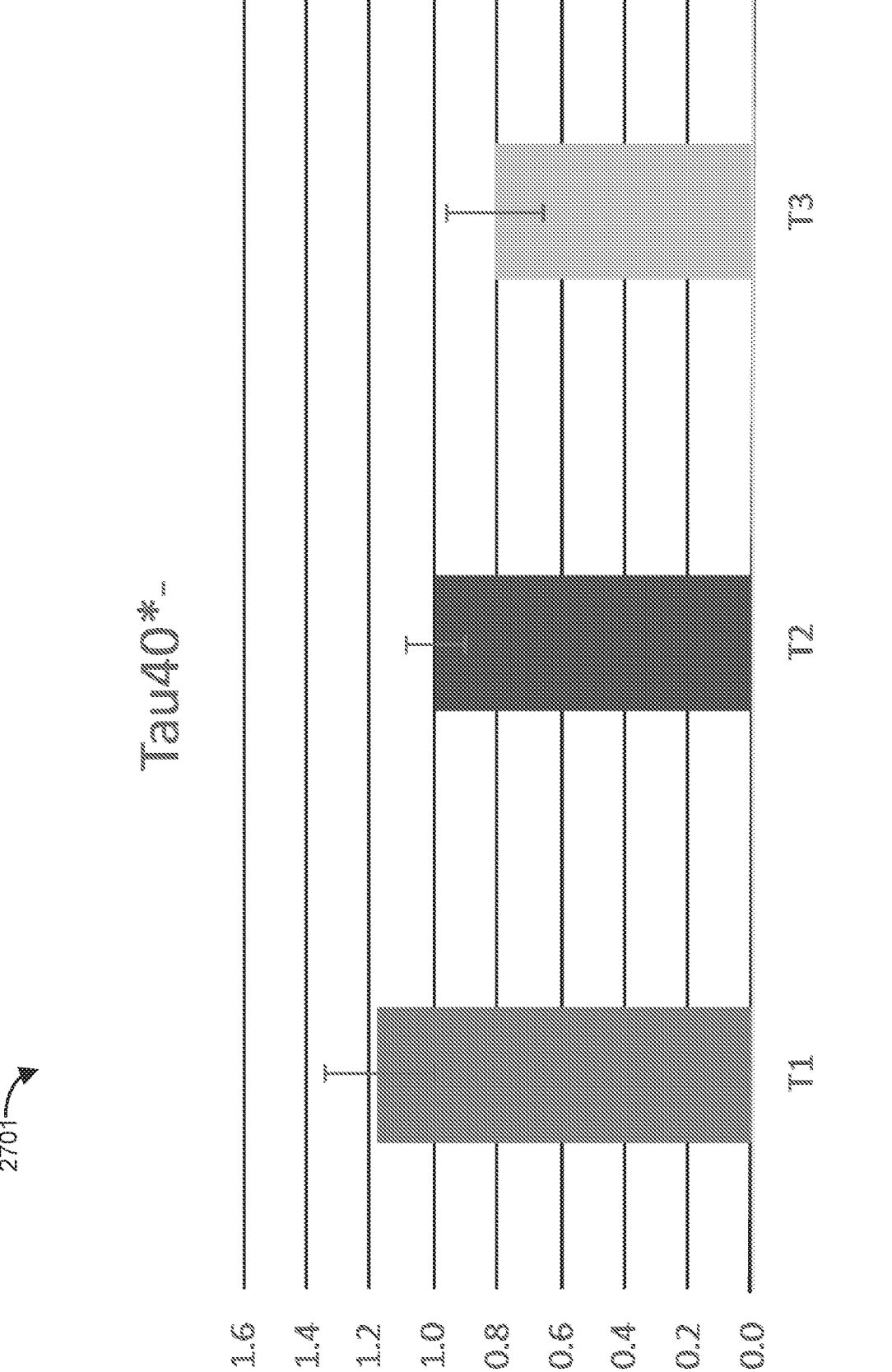

FIGS. 26A-B illustrate charts 2600 and 2601 comparing Tau and Tau40 calculations without heart rate compensation from a porcine non-clinical trial, in accordance with some embodiments of the present subject matter. FIGS. 27A-B illustrate charts 2700 and 2701 comparing Tau and Tau40 calculations with heart rate compensation from a porcine non-clinical trial, in accordance with some embodiments of the present subject matter. FIGS. 26 and 27 show that the Tau calculation depends on heart rate in test subject numbers 17-23 (7 Subjects). As described above, adjusting the Tau- value for heart beats, called Tau*, can create a reliable parameter to diagnose the increased damage of the myocardium. In addition, an adjusted Tau40-, known as Tau40*-, can be a very accurate parameter which correlates with MVO and the infarct.

Figure 28:
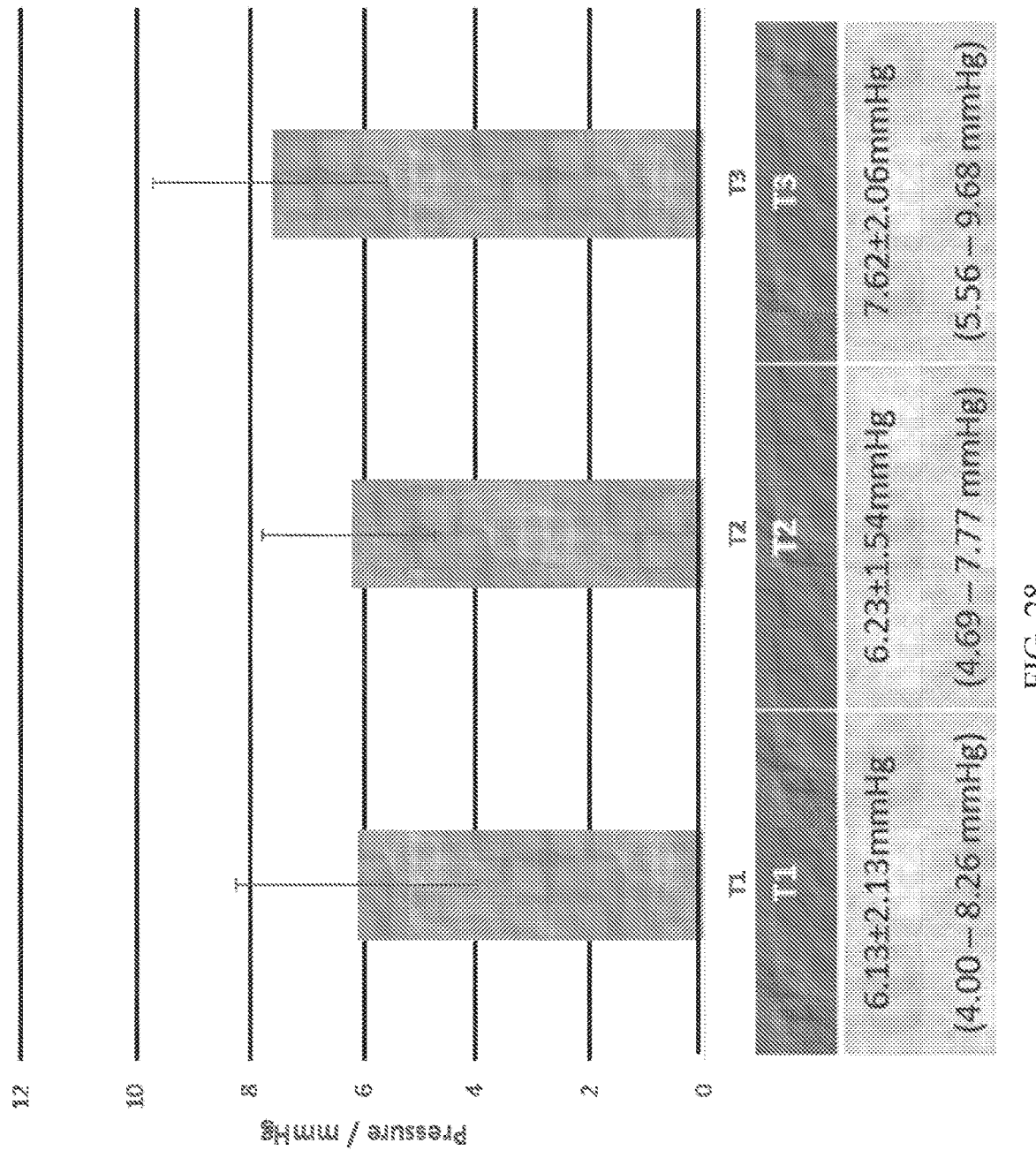
FIG. 28 illustrates a chart comparing waterfall pressure at T1, T2, and T3 from a porcine non-clinical trial, in accordance with some embodiments of the present subject matter.

FIG. 28 illustrates a chart 2800 comparing waterfall pressure at T1, T2, and T3 from a porcine non-clinical trial, in accordance with some embodiments of the present subject matter. The change in T3 is most likely caused by a different position of the occlusion balloon as the catheter was repositioned between T2 and T3. Chart 2800 graphs the waterfall pressure in test subject numbers 8-23 (15 subjects).

Figure 29:
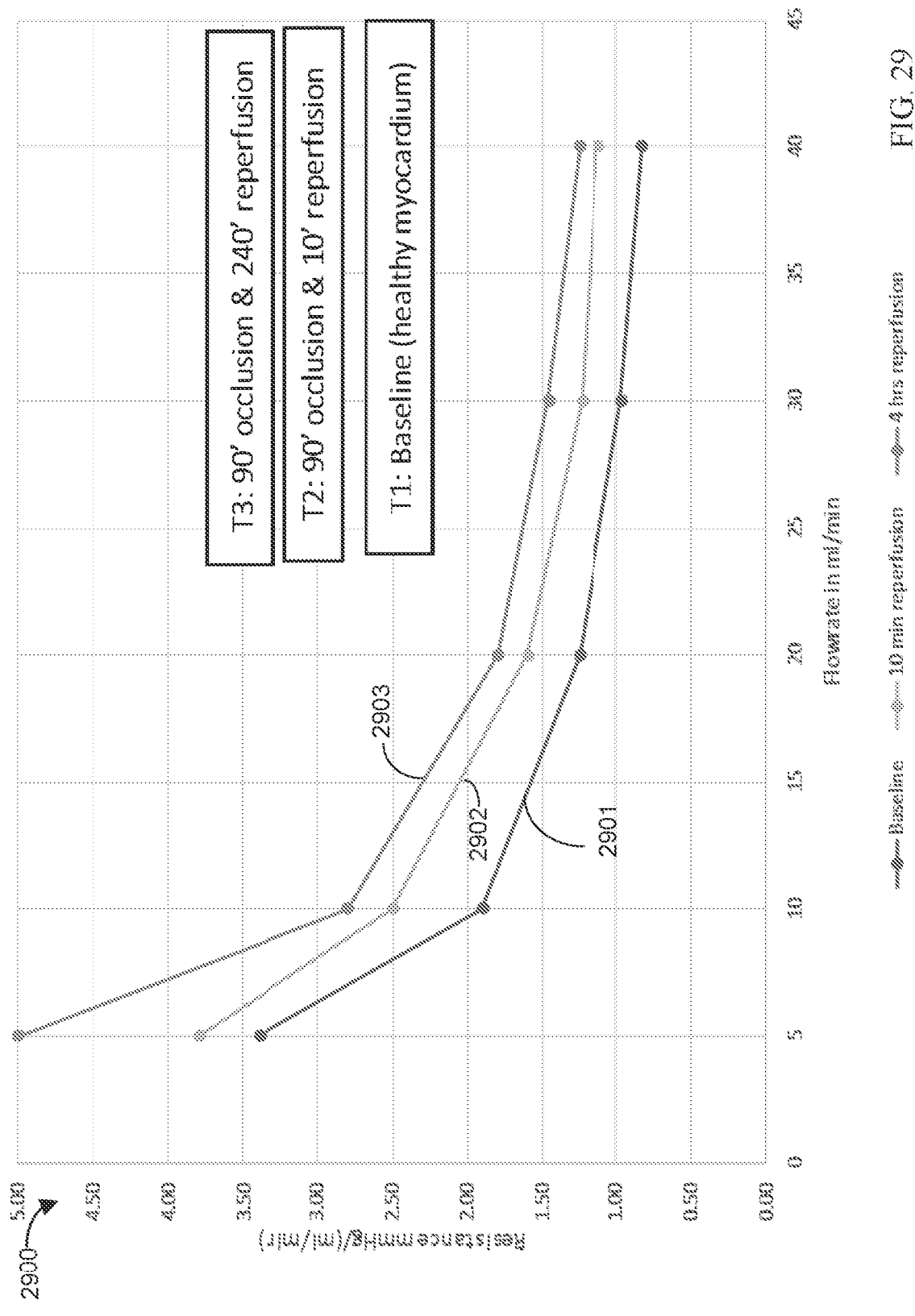
FIG. 29 illustrates a chart graphing real time vascular resistance from a porcine non-clinical trial, in accordance with some embodiments of the present subject matter.

FIG. 29 illustrates a chart 2900 graphing real time vascular resistance from a porcine non-clinical trial, in accordance with some embodiments of the present subject matter. The chart 2900 can be viewed in conjunction with FIG. 5 and graphs vascular resistance in real time with the baseline shown at 2901, the 10 minute reperfusion shown at 2902 and the four hour reperfusion shown at 2093. The baseline is a healthy myocardium. 2902 is an indication of T2 with a 90 minutes occlusion and a ten minutes reperfusion. 2903 is an indication of T3 with a 90 minutes occlusion and a four hour minute reperfusion.

Figure 30:
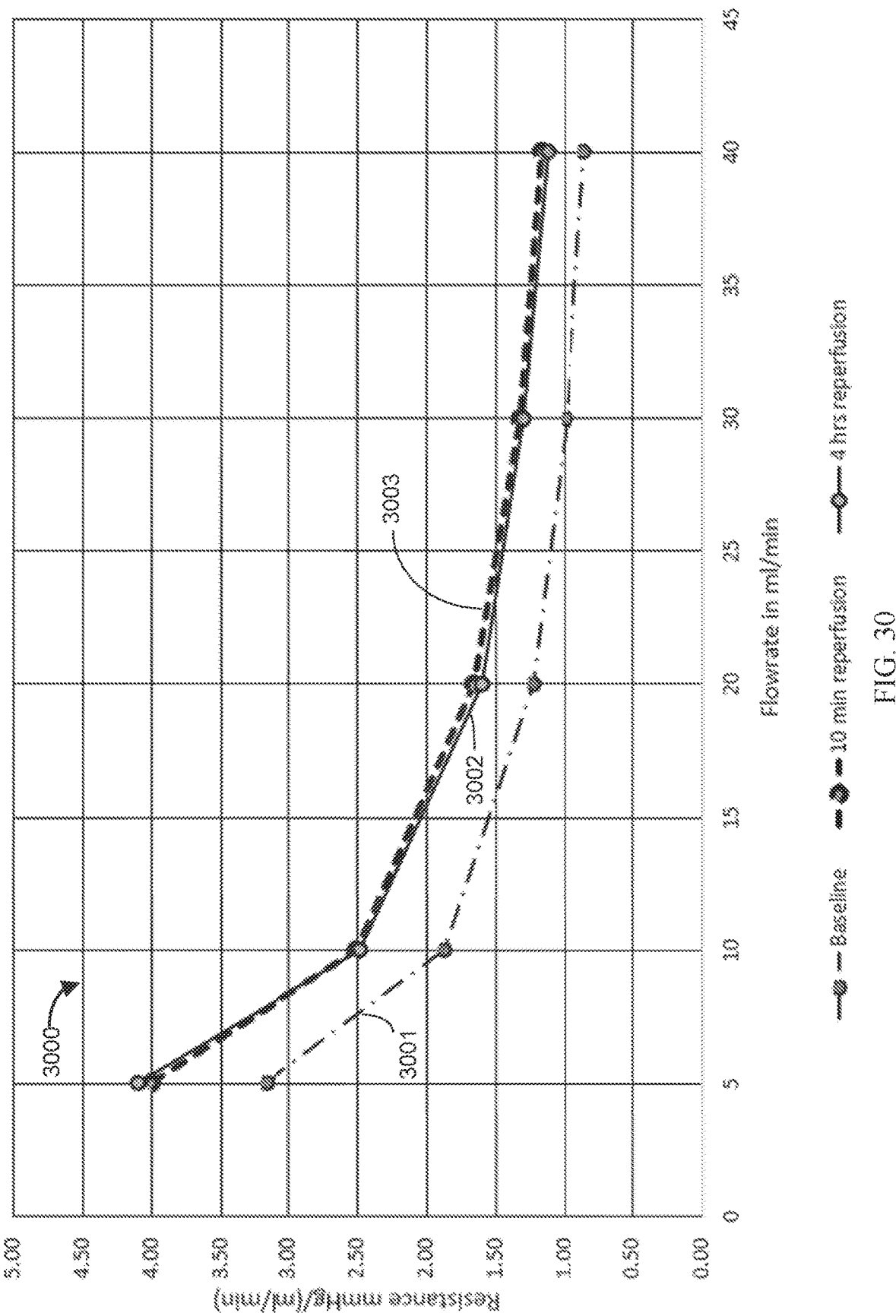
FIG. 30 illustrates a chart graphing mean values of real time vascular resistance from a porcine non-clinical trial in 7 subjects, in accordance with some embodiments of the present subject matter.

FIG. 30 illustrates a chart 3000 graphing mean values of real time vascular resistance from a porcine non-clinical trial in 7 subjects, in accordance with some embodiments of the present subject matter. Chart 3000 was made from results across seven test subjects (subject numbers 17-23). Baseline 3001, 10 minute reperfusion line 3002, and four hour reperfusion line 3003, are shown. The 10 minute reperfusion line 3002 and four hour reperfusion line 3003 track very closely with line 3002 being dashed.

Figure 31A:
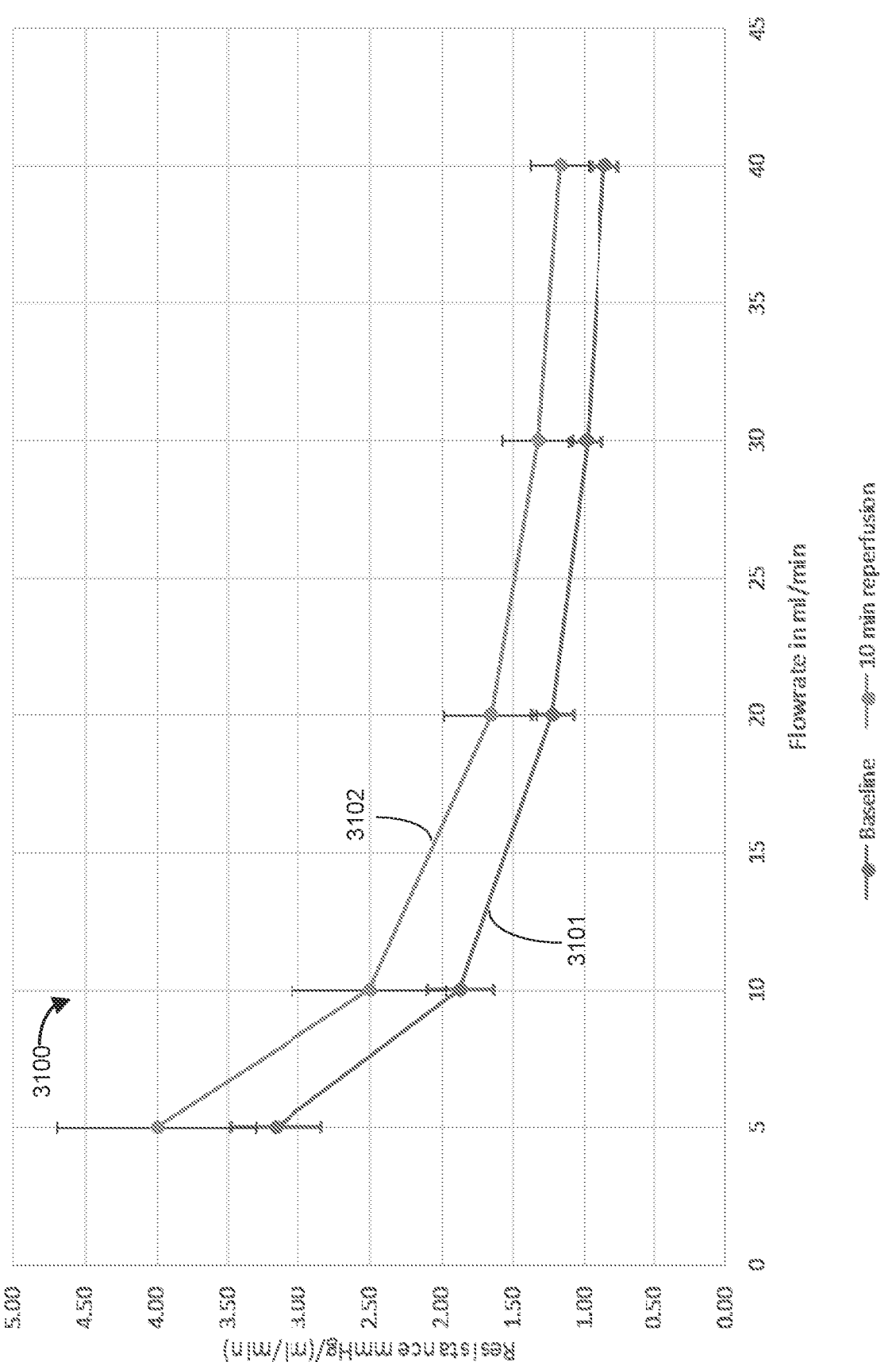
FIGS. 31A-B illustrate a chart graphing statistical significant difference across 7 subjects of real time vascular resistance from a porcine non-clinical trial with statistical significant difference for every flow infusion value, in accordance with some embodiments of the present subject matter.
Figure 31B:

FIGS. 31A-B illustrate a chart 3100 and a table 3104 showing statistical significant difference across 7 animals of real time vascular resistance from a porcine non-clinical trial with statistical significant difference for every flow infusion value, in accordance with some embodiments of the present subject matter. Baseline 3101 and 10 minute reperfusion line 3102 are shown. Chart 3100 and table 3104 were made from results across seven test subjects (subject numbers 17-23).

EXAMPLES

In Example 1, a method for analyzing microvascular obstruction (MVO), is provided. In various embodiments, the method may include receiving a first plurality of pressure measurements sensed distal of a blocking position in a vessel where antegrade blood flow in the vessel is substantially blocked and at least after a crystalloid solution is infused at one or more different flow infusion rates to the vessel distal of the blocking position. The method may include receiving a second plurality of pressure measurements configured to be taken after the infusion to the vessel is stopped and the antegrade blood flow in the vessel remains substantially blocked. The method may further include performing calculations at different times relating the one or more different flow infusion rates to the pressure measurements to determine a plurality of measurements related to vascular resistance at the different times.

In Example 2, the subject matter of claim 1 may further include measuring changes in the measurements related to vascular resistance associated with an infusion of a therapeutic solution.

In Example 3, the subject matter of Example 2 may further include determining a waterfall pressure at a plurality of the different times based on the pressure measurements. It may further include measuring changes in the waterfall pressure at the different times.

In Example 4, the subject matter of Example 3 may further include using an initial measurement of the vascular resistance and waterfall pressure as a baseline for determining a measure of therapeutic benefit of infusion of the therapeutic solution over time.

In Example 5, the subject matter of any of the preceding Examples 1-4 may include determining a plurality of dynamic microvascular resistance (dMVR) values based on dividing the pressure value by the different flow infusion rate at the different times.

In Example 6, the subject matter of any of Examples 3 or 4 may further include determining a plurality of dynamic microvascular resistance (dMVR) values based on dividing the pressure value by the flow infusion rate at the different times. The subject matter of Example 6 may further include compensating the dMVR using the waterfall pressure.

In Example 7, the subject matter of any of the Examples 5 or 6 may further include determining a change in a level of MVO using the plurality of dMVR values determined for the different times.

In Example 8, the subject matter of any of the preceding Examples 1 to 8 may further include determining a change in a level of MVO in real time over a time period.

In Example 9, the subject matter of Example 8 may further include determining a measure of efficacy of an applied therapy for treating MVO based on the change in the level of the MVO and dMVR over a time period.

In Example 10, the subject matter of any of the preceding Examples may further include wherein the vessel comprises a vessel supplying blood to a heart, and further comprising determining a change in a level of the vascular resistance for measuring change in a degree of myocardial infarction over a time period.

In Example 11, the subject matter of any of the preceding Examples 1-9 may further include wherein the vessel comprises a vessel supplying blood to a brain, and further comprising determining a change in a level of the vascular resistance for measuring change in a degree of stroke over a time period.

In Example 12, the subject matter of any of the preceding Examples 1-9 may further include wherein the vessel comprises a vessel supplying blood to an intestine, and further comprising determining a change in a level of the vascular resistance for measuring change in a degree of bowel ischemia or bowel infarction over a time period.

In Example 13 the subject matter of any of the preceding Examples 1-9 may further include wherein the vessel comprises a vessel supplying blood to a lung, and further comprising determining a change in a level of the vascular resistance for measuring change in a degree of pulmonary emboli or pulmonary infarction over a time period.

In Example 14, the subject matter of any of the preceding Examples 1-9 may further include wherein the vessel comprises a vessel supplying blood to a limb, and further comprising determining a change in a level of the vascular resistance for measuring change in a degree of critical limb ischemia or critical limb infarction over a time period.

In Example 15, the subject matter of any of the preceding Examples 1-9 may further include wherein the vessel comprises a vessel supplying blood to a kidney, and further comprising determining a change in a level of the vascular resistance for measuring change in a degree of renal ischemia or renal infarction over a time period.

In Example 16, the subject matter of any of the preceding Examples 1-9 may further include wherein the vessel comprises a vessel supplying blood to a liver, and further comprising determining a change in a level of the vascular resistance for measuring change in a degree of hepatic ischemia or hepatic infarction over a time period.

In Example 17, a system for measuring MVO in a body having an organ and a vessel supplying blood to the organ, wherein the system may include a percutaneous transvascular catheter a percutaneous transvascular catheter including an occlusion balloon suitable for blocking antegrade blood flow in the vessel, the catheter including a lumen configured for infusing an infusate to the vessel distal to the occlusion balloon and a sensor configured for sensing a blood pressure in the vessel distal to the occlusion balloon. The subject matter of Example 17 may further include a computerized diagnosis and infusion system configured to be coupled to the catheter to infuse multiple infusates and to: perform one or more measurements of the blood pressure at least after the infusate is infused to the vessel via the catheter at an infusate flow rate. It may further include a computerized diagnosis and infusion system configured to perform a calculation of the dynamic microvascular resistance at one of more calculations of the microvascular resistance at different times over a time period, the microvascular resistance being calculated by dividing the pressure measurement value by the value of infusate volume flow rate and over multiple volume flow rates and measured pressure values. It may further include a computerized diagnosis and infusion system configured to determine change in a level of the MVO over the time period based on at least the dynamic microvascular resistance measurement performed at the different times. It may further include a computerized diagnosis and infusion system configured to perform one or more measurements, perform the calculation of the dynamic microvascular resistance, and to determine a change in a level of the MVO. It may further include a computerized diagnosis and infusion system configured to be coupled to the catheter to infuse multiple infusates and to:

perform one or more measurements of the blood pressure at least after the infusate is infused to the vessel via the catheter at an infusate flow rate;

perform a calculation of the dynamic microvascular resistance at one of more calculations of the microvascular resistance at different times over a time period, the microvascular resistance being calculated by dividing the pressure measurement value by the value of infusate volume flow rate and over multiple volume flow rates and measured pressure values; and determine change in a level of the MVO over the time period based on at least the dynamic microvascular resistance measurement performed at the different times.

In Example 18, the subject matter of Example 17 may be configured such that the computerized diagnosis and infusion system is configured to infuse the infusate at the different times and to perform the one or more measurements and determine the change of the MVO over the time period in real time.

In Example 19, the subject matter of Example 18, further includes wherein the computerized diagnosis and infusion system is configured to determine the dynamic microvascular resistance by dividing the infusate pressure response by the infusate volume flow to produce a waterfall pressure, to adjust the dynamic microvascular resistance for the waterfall pressure, and to determine the change in the level of the MVO over the time period based on at least values of the dynamic microvascular resistance determined for the different times.

In Example 20, the subject matter of any one or any combination of Examples 17 to 19 may be configured wherein the computerized diagnosis and infusion system is configured to infuse the infusate at a plurality of increasing infusate flow rates In Example 21, another method for measuring MOV is provided. The method may include substantially blocking antegrade blood flow within a vessel supplying blood to an organ by inflating an occlusion balloon placed in the vessel; infusing an infusate to the vessel distal of the occlusion balloon at a plurality of increasing flow rates; sensing the pressure response to the different flow rates; calculating the dMVR; stopping the infusion of the infusate; sensing a blood pressure distal of the occlusion balloon in the vessel; measuring one or more parameters at least after the infusion of the infusate is stopped, the one or more parameters including a minimum pressure after a pressure decay (the waterfall pressure); treating the MVO by infusing a therapeutic infusate to the vessel distal of the occlusion balloon at different times over a therapeutic period, the therapeutic infusate flowing into any occluded portions of a vasculature distal of the occlusion balloon to promote mixing of the infusate with any obstructing matter in the vasculature; measuring the one or more parameters in real time at the different times during the therapeutic period; determining a result of the treatment of the MVO based on values of the one or more parameters measured in real time at the different times; and unblocking the antegrade blood flow within the vessel around said catheter by deflating the occlusion balloon.

In Example 22, the subject matter of measuring the one or more parameters as found in any one or any combination of Example 21 may optionally include measuring a pressure response being a change in the sensed blood pressure in response to the introduction of the infusate and calculating a real-time vascular resistance using the measured pressure response for each flow rate of the plurality of increasing flow rates, and the subject matter of determining the result of the treatment of the MVO as found in any one or any combination of Example 21 may optionally include comparing values of the real-time vascular resistance calculated for the different times during the therapeutic period.

In Example 23, the subject matter of Example 22 includes wherein measuring the one or more parameters comprises measuring the pressure decay parameter being a measure of time of an exponential decay of the sensed blood pressure after the introduction of the infusate is stopped.

In Example 24, the subject matter of Examples 21 to 23 includes compensating the dynamic microvascular resistance measurements with the measured waterfall pressure.

In Example 25, the subject matter of Examples 21 to 24 may optionally include measuring a heart rate and compensating the pressure decay parameter for the heart rate.

In Example 26, a method for measuring MVO is provided. The method may include performing one or more measurements of pressure in a vessel sensed distal of a blocking position where antegrade blood flow in the vessel is substantially blocked. The one or more measurements may be performed at least after an infusate is injected to the vessel distal of the blocking position at an infusate flow rate. The method may further include performing a pressure decay measurement of the one or more measurements of pressure at different times over a time period. The pressure decay measurement is related to time of decay of the pressure measured after the injection of the infusate is stopped and while the antegrade blood flow in the vessel remains substantially blocked. The method may further include determining change in a level of the MVO over the time period based on at least the pressure decay measurement performed at the different times.

In Example 27, the subject matter of Example 26 may optionally further include determining the change in the level of the MVO for measuring change in a degree of myocardial infarction over the time period. The vessel supplies blood to a heart.

In Example 28, the subject matter of Example 26 may optionally further include determining the change in the level of the MVO for measuring change in a degree of stroke over the time period. The vessel supplies blood to a brain.

In Example 29, the subject matter of Example 26 may optionally further include determining the change in the level of the MVO for measuring change in a degree of bowel ischemia or bowel infarction over the time period. The vessel supplies blood to an intestine.

In Example 30, the subject matter of Example 26 may optionally further include determining the change in the level of the MVO for measuring change in a degree of pulmonary emboli or pulmonary infarction over the time period. The vessel supplies blood to a lung.

In Example 31, the subject matter of Example 26 may optionally further include determining the change in the level of the MVO for measuring change in a degree of critical limb ischemia or critical limb infarction over the time period. The vessel supplies blood to a limb.

In Example 32, the subject matter of Example 26 may optionally further include determining the change in the level of the MVO for measuring change in a degree of renal ischemia or renal infarction over the time period. The vessel supplies blood to a kidney.

In Example 33, the subject matter of Example 26 may optionally further include determining the change in the level of the MVO for measuring change in a degree of hepatic ischemia or hepatic infarction over the time period. The vessel supplies blood to a liver.

In Example 34, the subject matter of determining the change in the level of the MVO over the time period as found in any one or any combination of Examples 26 to 33 may optionally include determining a time constant (Tau) based on the pressure decay measurement and determining the change in the level of the MVO over the time period based on values of the Tau determined for the different times. The Tau is a measure of time of an exponential decay of the pressure.

In Example 35, the subject matter of any one or any combination of Examples 26 to 34 may optionally further include injecting the infusate to the vessel distal of the blocking position. The infusate includes a ringer solution.

In Example 36, the subject matter of Example 35 may optionally further include injecting the ringer solution at a plurality of increasing infusate flow rates.

In Example 37, the subject matter of determining the Tau as found in any one or any combination of Examples 24 to 36 may optionally include producing a heart rate and compensating the Tau for the heart rate.

In Example 38, the subject matter of any one or any combination of Examples 26 to 37 may optionally further include performing the one or more measurements and determining the change in the level of the MVO in real time over the time period.

In Example 39, the subject matter of any one or any combination of Examples 26 to 38 may optionally further include applying a therapy treating the MVO over the time period and determining efficacy of the therapy based on the change in the level of the MVO over the time period.

In Example 40, the subject matter of any one or any combination of Examples 26 to 39 may optionally further include performing a resistance measurement of the one or more measurements of pressure at the different times over the time period, and the subject matter of determining the change in the level of the MVO over the time period as found in any one or any combination of Examples 26 to 39 may optionally further include determining an intravascular resistance based on the resistance measurement and determining the change in the level of the MVO over the time period based on values of the intravascular resistance determined for the different times.

The foregoing examples are not limiting or exclusive, and the scope of the present subject matter is to be determined by the specification as a whole, including the claims and drawings.

The above description includes references to the accompanying drawings, which form a part of the detailed description. The drawings show, by way of illustration, varying embodiments in which the invention can be practiced. The application also refers to "examples." Such examples can include elements in addition to those shown or described. The foregoing examples are not intended to be an exhaustive or exclusive list of examples and variations of the present subject matter.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The scope of the invention should be determined with reference to the appended claims, along with the full scope of equivalents to which such claims are entitled.

What is claimed is:

1. A system for measuring microvascular obstruction (MVO) in a body having an organ and a vessel supplying blood to the organ, the system comprising:
   a percutaneous transvascular catheter including:
      an occluder disposed on a distal portion of the percutaneous transvascular catheter and configured to be disposed in the vessel to block antegrade blood flow in the vessel; and
      a lumen having an outlet disposed distal to the occluder and configured to discharge infusate into the vessel distal to the occluder;
   a pressure sensor configured to sense a blood pressure in the vessel distal to the occluder;

an infusion pump coupleable to the lumen of the catheter and configured to infuse an infusate into the vessel distal to the occluder via the lumen; and a computerized system coupled to the pressure sensor and to the infusion pump and configured to:

cause the infusion pump to infuse an infusate into the vessel distal to the occluder at a first mean infusate flow rate for a first infusion time;

cause the infusion pump to infuse an infusate into the vessel distal to the occluder at a second mean infusate flow rate, greater than the first mean infusate flow rate, for a second infusion time;

measure the blood pressure in the vessel distal to the occluder with the pressure sensor at multiple points in time at least during each of the first infusion time and the second infusion time;

calculate a value of dynamic microvascular resistance at each of the multiple points in time by:

dividing a value of the blood pressure at each of the multiple points in time during the first infusion time by the first mean infusate flow rate; and dividing the value of the blood pressure at each of the multiple points in time during the second infusion time by the second mean infusate flow rate; and determine a change in a level of the MVO over the first infusion time and the second infusion time based on at least the value of the dynamic microvascular resistance calculated at each of the multiple points in time.

2. The system of claim 1, wherein the computerized system is configured to calculate the value of the dynamic microvascular resistance at each of the multiple points in time and to determine the change in the level of the MVO in real time.

3. The system of claim 2, wherein the computerized system is configured to determine a waterfall pressure and to adjust the calculation of the value of the dynamic microvascular resistance at each of the multiple points in time for the waterfall pressure.

4. The system of claim 1, wherein the occluder is a balloon.

5. The system of claim 1, wherein the pressure sensor is disposed distal to the occluder.

6. The system of claim 5, wherein the pressure sensor is a pressure measuring guidewire.

7. The system of claim 1, wherein the first mean infusate flow rate during the first infusion time is approximately constant and the second mean infusate flow rate during the second infusion time is approximately constant.

8. The system of claim 1, wherein the computerized system is further configured to:

cause the infusion pump to infuse an infusate into the vessel distal to the occluder at a third mean infusate flow rate, greater than the second mean infusate flow rate, for a third infusion time;

measure the blood pressure in the vessel distal to the occluder with the pressure sensor at multiple points in time at least during the third infusion time;

calculate a value of dynamic microvascular resistance at each of the multiple points in time during the third infusion time by dividing a value of the blood pressure measurement at each of the multiple points in time during the third infusion time by the third mean infusate flow rate; and determine a change in a level of the MVO over the first infusion time, the second infusion time, and the third infusion time based on at least the value of the dynamic microvascular resistance calculated at each of the multiple points in time.

9. The system of claim 8, wherein the third mean infusate flow rate during the third infusion time is approximately constant.

10. The system of claim 1, wherein the organ is a heart and the vessel is a coronary artery.

* * * * *